(12) United States Patent
Cole et al.

(10) Patent No.: US 8,772,229 B2
(45) Date of Patent: Jul. 8, 2014

(54) METHODS FOR SYNTHESIS AND USES OF INHIBITORS OF GHRELIN O-ACYLTRANSFERASE AS POTENTIAL THERAPEUTIC AGENTS FOR OBESITY AND DIABETES

(75) Inventors: Philip A. Cole, Baltimore, MD (US); Bradley P. Barnett, Baltimore, MD (US); Yousang Hwang, Baltimore, MD (US); Jef D. Boeke, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 351 days.

(21) Appl. No.: 13/122,438

(22) PCT Filed: Sep. 18, 2009

(86) PCT No.: PCT/US2009/057512
§ 371 (c)(1),
(2), (4) Date: Apr. 4, 2011

(87) PCT Pub. No.: WO2010/039461
PCT Pub. Date: Apr. 8, 2010

(65) Prior Publication Data
US 2011/0257086 A1    Oct. 20, 2011

Related U.S. Application Data

(60) Provisional application No. 61/102,549, filed on Oct. 3, 2008.

(51) Int. Cl.
*A61K 38/00* (2006.01)
*A61P 3/04* (2006.01)
*A61K 38/28* (2006.01)
*A61P 3/10* (2006.01)
*A61P 7/12* (2006.01)
*A61K 38/08* (2006.01)
*A61K 38/10* (2006.01)
*A61K 38/16* (2006.01)
*C07K 5/00* (2006.01)
*C07K 7/00* (2006.01)
*C07K 16/00* (2006.01)
*C07K 17/00* (2006.01)
*A61K 38/04* (2006.01)

(52) U.S. Cl.
USPC ......... 514/4.8; 514/21.3; 514/21.4; 514/21.5; 514/6.9; 530/324; 530/325; 530/326; 530/327

(58) Field of Classification Search
CPC ..................................................... A61K 38/00
See application file for complete search history.

(56) References Cited

U.S. PATENT DOCUMENTS

2010/0086955 A1    4/2010    Harran

FOREIGN PATENT DOCUMENTS

WO    WO-2007/041278 A2    4/2007

OTHER PUBLICATIONS

Yang J et al "Inhibition of ghrelin O-acytransferase (GOAT) by octanoylated pentapeptides" Proc Natl Acad Sci 105:10750-10755. Published Aug. 5, 2008.*
Masayasu Kojima and Kenji Kangawa, "Ghrelin: Structure and Function", Physiological Reviews, vol. 85, pp. 495-522 (2005).
Jing Yang et al., "Inhibition of ghrelin O-acyltransferase (GOAT) by octanoylated pentapeptides", PNAS, vol. 105(31), pp. 10750-10755 (Aug. 5, 2008).
Oreste Gualillo et al., "Introducing GOAT: a target for obesity and anti-diabetic drugs?" Trends in Pharmacological Sciences, vol. 29(8), pp. 398-401 (published online Jul. 6, 2008).
International Search Report and Written Opinion in PCT/US2009/057512 Mailed Apr. 30, 2010.
B. P. Barnett, et al., "Glucose and Weight Control in mice with a Designed Ghrelin O-Acyltransferase Inhibitor", Science, vol. 330, No. 6011, Dec. 17, 2010, pp. 1689-1692.

* cited by examiner

*Primary Examiner* — Maury Audet
*Assistant Examiner* — Zachary J Miknis
(74) *Attorney, Agent, or Firm* — Venable LLP; Stefan J. Kirchanski

(57) ABSTRACT

The invention provides inhibitors of ghrelin O-acyltransferase, and methods of making and using them. In some embodiments, the invention provides bisubstrate analog inhibitors of ghrelin O-acyltransferase, which can be effective in treating, for example, obesity and diabetes mellitus.

17 Claims, 14 Drawing Sheets

|  | D4-Tat | GO-CoA-Tat |
|---|---|---|
| Cholesterol (mg/dl) | 131.7 +/- 8.7 | 155.3 +/- 11.6 |
| High-density lipoprotein (mg/dl) | 65.3 +/- 4.1 | 76.3 +/- 4.9 (p<.05) |
| Low-density lipoprotein (mg/dl) | 53.1 +/- 7.5 | 61.9 +/-7.6 |
| Triglycerides (mg/dl) | 66.6 +/- 3.1 | 85.3 +/- 8.5 (p<.05) |
| Uric Acid (mg/dl) | 2.6 +/- 0.6 | 2.5 +/- 0.4 |
| Creatine kinase (U/L) | 116.3 +/- 45.8 | 544.3 +/- 705.6 |
| Alanine Aminotransferase (U/L) | 19.3 +/- 1.2 | 43.1 +/- 31.2 |
| Aspartate Aminotransferase (U/L) | 40.3 +/- 20.5 | 164 +/- 174.3 |
| Amylase (U/L) | 1309.3 +/- 393.7 | 1937.3 +/- 1291.6 |
| Lactate deyhdrogenase (U/L) | 127 +/- 25.9 | 287.3 +/- 202.8 |
| Alkaline Phosphatase (U/L) | 66.7 +/- 28.9 | 74.6 +/- 4.6 |
| Total Billirubin (mg/dl) | 0.2 +/- 0.1 | 0.23 +/- 0.06 |
| Glucose (mg/dl) | 246.3 +/- 21.1 | 268.6 +/- 75.8 |
| Total Protein (g/dl) | 5.4 +/- 0.3 | 5.7 +/- 0.4 |
| Calcium (mg/dl) | 7 +/- 4.5 | 9.7 +/- 0.6 |
| Blood Urea Nitrogen (mg/dl) | 20.3 +/- 5.9 | 19.7 +/- 3.1 |
| Creatinine (mg/dl) | 0.3 +/- 0.1 | 0.33 +/- 0.1 |
| Albumin (g/dl) | 3.1 +/- 0.1 | 3.3 +/- 0.3 |
| White blood cells (K/μL) | 5.1 +/- .8 | 6.34 +/- 3.0 |
| Neutrophils (K/μL) | 0.85 +/- .1 | 1.4 +/- 0.8 |
| Lymphocytes (K/μL) | 4.1 +/- .9 | 4.7 +/- 2.8 |
| Monocytes (K/μL) | 0.22 +/- .03 | 0.17 +/- 0.12 |
| Eosinophils (K/μL) | 0.05 +/- .03 | 0.07 +/-0 .04 |
| Basophils (K/μL) | 0.01 +/- .01 | 0.02 +/- 0.03 |
| Red blood cells (M/μL) | 9.2 +/- .2 | 9.4 +/- 0.4 |
| Hemoglobin (g/dL) | 13.5 +/- .4 | 13.8 +/- 0.9 |
| Hematocrit (%) | 42.5 +/- .9 | 43.6 +/- 2.8 |
| Mean corpuscular volume (fL) | 46.1 +/- .5 | 46.5 +/- 0.8 |
| Mean corpuscular hemoglobin (pg) | 14.7 +/- .06 | 14.8 +/- 0.3 |
| Mean cell hemoglobin conc. (g/dL) | 31.9 +/- .4 | 31.8 +/- 0.4 |
| Red blood cell distribution width (%) | 17.4 +/- .06 | 17.2 +/- 0.3 |
| Platelets (K/μL) | 779.3 +/- 46.4 | 607 +/-309.3 |
| Mean platelet volume (fl) | 4.7 +/- 0.2 | 5.1 +/- 0.8 |

Figure 9

METHODS FOR SYNTHESIS AND USES OF INHIBITORS OF GHRELIN O-ACYLTRANSFERASE AS POTENTIAL THERAPEUTIC AGENTS FOR OBESITY AND DIABETES

Research described in this application was supported by grants U54 RR020839 and R01 AG19186 from the National Institutes of Health. The United States Government has certain rights in this application.

This application is a National Stage entry under 35 U.S.C. §371 of Application No. PCT/US2009/057512, filed Sep. 18, 2009, which claims priority to U.S. Provisional Application No. 61/102,549, filed Oct. 3, 2008. Each of these applications is hereby incorporated by reference in its entirety and for all purposes.

FIELD OF THE INVENTION

The invention relates to inhibitors of ghrelin O-acyltransferase, and methods of making and using them.

BACKGROUND

The persistent rise in the proportion of overweight individuals in Western society over the past 30 years has been associated with substantial excess morbidity and is widely recognized as a major public health concern. To address this problem, intensive efforts exist to clarify neuroendocrine contributions to weight gain. Starting with the isolation of leptin (1), a series of hormones acting centrally and peripherally to influence body mass have been discovered. Among these, the gastric peptide hormone acyl-ghrelin has generated considerable interest as an important stimulus for weight gain (2-5) and modulator of glucose homeostasis (6-8). Various strategies in therapeutic development have been described for the antagonism of acyl-ghrelin (9), although none has yet emerged as clinically beneficial.

The biosynthesis of acyl-ghrelin involves an unusual post-translational octanoylation of the serine at the 3 position of the ghrelin peptide. This octanoylation is necessary for its bioactivity, which occurs via interaction with the growth hormone secretagogue receptor (GHSR). The enzyme responsible for this esterification, ghrelin O-acyltransferase (GOAT), has recently been cloned (10, 11).

There remains a need in the art for improved therapeutic agents for use in the treatment of obesity and diabetes, especially ones that target neuroendrocrine pathways. In countering the global pandemic of obesity, which causes an estimated 10,000 premature deaths per week, an effective appetite-reduction medication can be potentially life-saving on a grand scale.

SUMMARY

The present inventors have found that an inhibitor of GOAT can induce satiety and weight reduction in the obese patient. Furthermore, blocking acylated ghrelin can improve the glucose responsiveness of islets, and thus a GOAT inhibitor is also expected to be an effective therapeutic for use in the Type II diabetic patient population.

These and other objects are achieved by providing a bisubstrate analog ghrelin O-acyltransferase (GOAT) inhibitor, such as, for example, GO-CoA-Tat, which is potent, selective, and effective in vitro, in cell culture, and in mice. Administration of compounds such as GO-CoA-Tat enhances insulin response to a glucose load and leads to a statistically significant weight loss in subjects fed a high fat diet. Treatment with, for example, GO-CoA-Tat also leads to selective reduction in fat versus lean mass.

In one aspect, the invention provides compounds that can inhibit membrane-bound O-acyltransferase (mBOAT) membrane proteins, such as ghrelin O-acyltransferase. In some embodiments, the compounds are of the formula

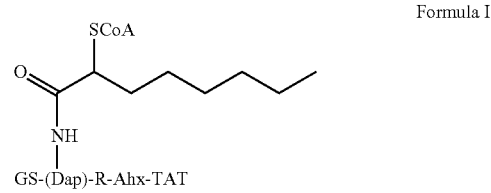

Formula I

GS-(Dap)-R-Ahx-TAT wherein SEQ ID NO:1 represents the general sequence for the GS to TAT peptide when R is a peptide and wherein R is absent, or is an organic moiety selected from the group consisting of a substituted or unsubstituted alkyl group, a substituted or unsubstituted peptide chain, a substituted or unsubstituted polysaccharide, or a peptoid residue such as, for example, N-methyl or other N-alkyl substituted glycine. If R is a peptide chain, it can be, for example, a chain of 1-20 amino acid residues. In some embodiments, R is a peptide chain corresponding to ghrelin residues 4-28 (in this case the GS to TAT sequence is SEQ ID NO:25), or 4-15 (in this case the GS to TAT sequence is SEQ ID NO:23), or 4-10 (in this case the GS to TAT sequence is SEQ ID NO:22), or 4-5 (in this case the GS to TAT sequence is SEQ ID NO:24).

As used herein, "amino acid" includes both naturally occurring and synthetic amino acids. These include, inter alia, alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ε-N-methyllysine, ε-N,N,N-trimethyllysine, aminoadipic acid, γ-carboxyglutamic acid, phosphoserine, phosphothreonine, phosphotyrosine, N-methylarginine, and N-acetyllysine. Both R and L forms and mixed R and L forms of alpha amino acids are contemplated. Further possible substituents include amino acids that have 2 or more —CH$_2$— groups (usually 2-4) present between the amino and carboxyl groups, and derivatives thereof. Thus, the amino acid residue may be the residue of an alpha, beta, gamma, or higher order amino acid, preferably one corresponding to a naturally occurring amino acid in other respects. As used herein, "amino acid residue" encompasses, for example, any amino acid listed above when incorporated into, e.g., an amino acid sequence or other chain structure, whether such chain is linear or branched.

In another aspect, the invention provides compositions. For example, a composition can comprise a compound of the invention and a pharmaceutically acceptable excipient or carrier.

In still another aspect, the invention provides methods for preparing the compounds of the invention. For example, the method can comprise the steps of providing a ghrelin peptide sequence comprising from 3 to 15 N-terminal amino acid residues, wherein the serine residue at the 3 position is replaced with alloc-protected 1,2-diaminopropionic acid and wherein D4-Tat ("D4" disclosed as SEQ ID NO: 2) is bound to one end of the peptide sequence; combining the ghrelin peptide sequence with Pd(PPh$_3$)$_4$ palladium reagent, n-bromo octanoic anhydride and Reagent K in one or more reaction vessels to obtain a bromo-octanoylated intermediate; and combining the bromo-octanoylated intermediate with coenzyme A.

In yet another aspect, the invention provides methods for treating a disease, disorder or condition using the compounds and compositions of the invention. In some embodiments, the methods are used to treat obesity. These methods can comprise administering to a subject a composition comprising a therapeutically effective amount of one or more of the compounds of the invention. The methods can, for example, bring about a greater loss of fat mass than lean mass in the subject, or they can bring about an increase in the ratio of ghrelin to acyl-ghrelin in the subject. In some embodiments, the methods can be used to treat diabetes, for example type II diabetes. These methods can comprise administering to a subject a composition comprising a therapeutically effective amount of one or more of the compounds of the invention. These methods can, for example, bring about an increased production of insulin in the subject, or an increased responsiveness to a glucose challenge in the subject, or a reduction in uncoupling-protein 2 (UCP-2) mRNA levels in the subject. In some embodiments, the methods can be used to treat irritable bowel syndrome. These methods can comprise administering to a subject a composition comprising a therapeutically effective amount of one or more of the compounds of the invention.

In another aspect, the invention provides methods for treating mBOAT-associated diseases. In some embodiments, these methods can comprise administering to a subject a composition comprising a therapeutically effective amount of one or more compounds of the invention.

In yet another aspect, the invention provides kits. For example, the kits can comprise a composition comprising at least one dose of a therapeutically effective amount of the compounds and compositions disclosed herein. In some embodiments, the kits also include at least one dose of an additional weight loss treatment.

BRIEF DESCRIPTION OF THE DRAWINGS

FIG. 1B discloses SEQ ID NOS: 2, 3, 27, 28, 29 and 22, respectively, in order of appearance. (C) Structures of compounds according to the present invention. FIG. 1C discloses SEQ ID NOS: 22-24 and 30-33, respectively in order of appearance. (D) Dose-response reduction of acyl-ghrelin levels by GO-CoA-Tat in HEL cell lysate (2.5×106 cells) after 24 hr incubation. (E) Temporal inhibition of 2 µM GO-CoA-Tat in HEL cell lysate (2.5×106 cells). (F) In vitro assay for ghrelin-O-acyltransferase (GOAT) is inhibited by 100 nM GO-CoA-Tat. (G) Acyl-ghrelin levels (pg/ml) in HEL cell lysate (2.5×106 cells) after 24 hr incubation with one of the seven compounds listed in FIG. 1C.

FIG. 9: Blood panel from mice treated with D4-Tat ("D4" disclosed as SEQ ID NO: 2) and GOCoA-Tat. Samples taken at 2 pm after 12 days of daily compound administration demonstrated a statistically significant increase in high density lipoprotein (p=0.04) and triglycerides (p=0.02) for GO-CoA-Tat mice as compared to D4-Tat ("D4" disclosed as SEQ ID NO: 2) treated mice. No other differences in values were found to be statistically significant between the two groups. Figures disclose "D4" disclosed as SEQ ID NO: 2.

DETAILED DESCRIPTION

Figure 1:
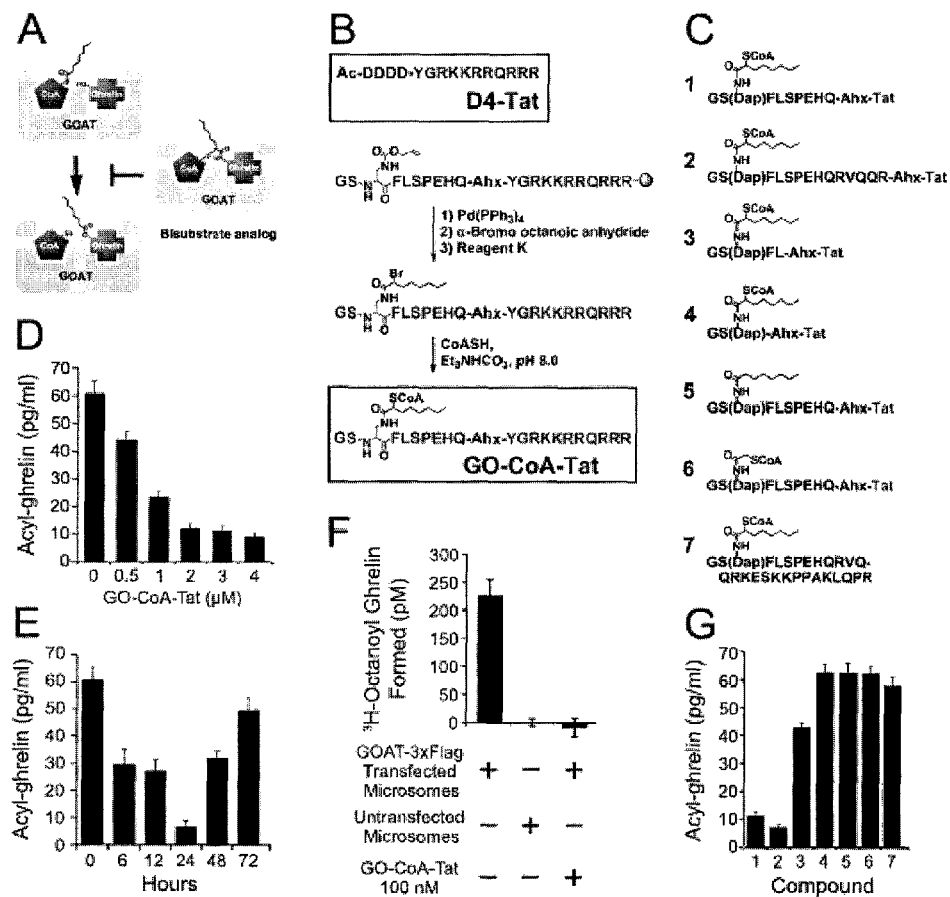
FIGS. 1A-1G: GO-CoA-Tat is a bisubstrate inhibitor that inhibits GOAT, lowering acyl ghrelin levels. (A) Bisubstrate analog inhibitors covalently combine two substrates, thereby increasing potency and specificity. (B) Structure of D4-Tat ("D4" disclosed as SEQ ID NO:2) and synthetic scheme for bisubstrate inhibitors, which consist of three components or their substantial equivalents: coenzyme A; an octanoylated moiety such as, for example, a substituted or unsubstituted ghrelin peptide; and a Tat peptide.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference, in their entirety and for all purposes, as if each had been individually incorporated.

Compounds

Ghrelin, a powerful appetite-stimulating hormone secreted by the stomach, has been implicated as a key peptide hormone that stimulates weight gain in animals and people. To exert its effects, ghrelin requires acylation, an unusual post-translational octanoylation of the serine residue at the 3 position. The octanoylated form of ghrelin is commonly referred to as acyl-ghrelin.

The octanoylation of ghrelin is mediated by ghrelin O-acyltransferase (GOAT). GOAT is a member of the membrane-bound O-acyltransferase (mBOAT) family of membrane proteins. Disclosed herein is a bisubstrate analog GOAT inhibitor, GO-CoA-Tat, which is potent, selective, and effective in vitro, in cell culture, and in mice.

In some embodiments, the invention provides compounds for use in treating, for example, obesity and/or diabetes. The compounds can have the generic formula (I) (SEQ ID NO: 1):

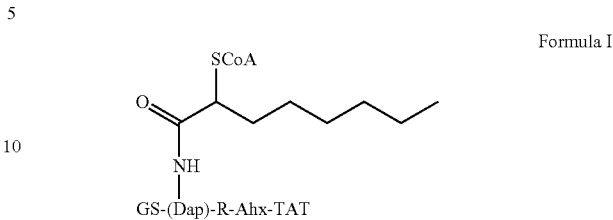

Formula I

In formula I, R may be absent, or R can be any organic moiety consistent with the proper functioning of the compound, as disclosed herein. R can be, for example, an alkyl group, as well as combinations of peptoid residues (e.g., N-alkyl Gly), beta amino acids, aminobutyrate, and phenylGly. In some embodiments, R is a peptide chain made up of amino acid residues, such as, for example, those comprising a fragment of the ghrelin peptide. The fragment of the ghrelin peptide can begin, for example, at residue 4. R can be made up, for example, of residues 4-5 (SEQ ID NO: 24), or 4-10 (SEQ ID NO: 22), or 4-15 (SEQ ID NO: 23), or 4-28 (SEQ ID NO: 25) of the ghrelin peptide. Indeed, the invention contemplates that R can be any number of residues that is capable of functioning according to the invention as disclosed herein. The compound of formula I is also referred to as "GO-CoA-Tat." In addition, specific examples of compounds that fall within the genus defined by Formula I can also be referred to as "GO-CoA-Tat." GO-CoA-Tat is an inhibitor of GOAT, which mediates the octanoylation of ghrelin to produce acyl-ghrelin.

In formula I, the moiety designated "GS" is made up of the amino acid residues corresponding to glycine and serine, respectively, according to their conventional one-letter designations. The glycine and serine can be substituted with any organic moiety, including a peptide chain of any length, that can function according to the invention as disclosed herein. Examples of suitable substitutes for the serine residue include, for example, D-amino acids such as D-Ala or D-Ser, which can also be truncated to an acetyl, or propionyl group; or a hydroxyacetyl substituent. Examples of suitable substitutes for the glycine residue include those listed for serine as well as a peptoid residue (e.g., N-alkyl Gly), a beta amino acid, aminobutyrate, and phenylGly. As used herein, "peptide chain" encompasses moieties that include peptoid residues and other variants or derivatives of amino acids; it also encompasses moieties made of combinations of naturally occurring amino acids, peptoid residues and other amino acid variants or derivatives, or any subset thereof.

"Dap" refers to 1,2-diaminopropionic acid. Where GS-Dap-R is derived from the N-terminal end of the ghrelin peptide, Dap replaces the serine normally present at the 3 position. Dap is a serine isostere with a nitrogen in place of oxygen in the side chain, leading to an amide linkage. "Ahx" refers to an amino-hexanoyl linker, which is used to link R with the Tat sequence. Ahx can be, for example, aminohexanoic acid, glycine, amino propionic acid, amino butyric acid, aminopentanoic acid, and ethyleneglycol-based substituents.

"Tat," which is shorthand for "trans-acting activator of transcription," refers to a peptide sequence commonly found in the HIV virus. For example, "Tat" can be an 11-residue peptide comprising the amino acids YGRKKRRQRRR (SEQ ID NO: 3). Tat proteins can mediate the transport of molecules, such as proteins or other moieties, across cell membranes. Such mediation appears to be independent of molecule size and does not appear to involve any disruption of the plasma membrane. Without wishing to be bound by any particular theory, it is hypothesized that the Tat moiety in GO-CoA-Tat aids in the delivery of the compound into the interior of the cell. Accordingly, any moiety that would also aid in such delivery can be substituted for Tat in the compounds of the present invention. Examples of suitable substituents for Tat include, for example, oligoArg, oligoalkyl guanidiniums, and either d- or l-stereoisomers for Tat. "D4-Tat," ("D4" disclosed as SEQ ID NO: 2) as used herein, comprises a peptide of four aspartate residues bound to a Tat sequence. D4-Tat ("D4" disclosed as SEQ ID NO: 2) were prepared using the Fmoc strategy or a modification thereof.

Without wishing to be bound by any particular theory, the design of GO-CoA-Tat is based on the theory that, if GOAT uses a ternary complex mechanism which templates octanoyl-CoA and ghrelin peptide, linking the two substrates with a non-cleavable bridge could combine the binding energies of the individual ligands without the entropic loss associated with forming the ternary complex (FIG. 1A). A related successful strategy has been used for other peptide-modifying enzymes, including histone acetyltransferases (HAT) and protein kinases. Because, where ghrelin peptide is used as the R group in Formula I, we were uncertain about the ghrelin peptide length needed for recognition by GOAT, we selected amino acids 1-10 for coupling to octanoyl-CoA, to maximize inclusion of highly conserved ghrelin residues. An Tat-derived peptide sequence, for example an 11-mer HIV Tat, can also be attached to the C-terminus via an amino-hexanoyl linker to enhance cell penetration.

At the outset of this work, an in vitro GOAT assay had not yet been developed so we investigated the effects of GO-CoA-Tat on acyl-ghrelin production in three cell types. We employed D4-Tat ("D4" disclosed as SEQ ID NO: 2) (tetra-aspartate, or DDDD (SEQ ID NO: 2), to simulate the negative CoA charge, similarly linked to the Tat peptide) as a control. In each of three cell lines tested, levels of acyl-ghrelin, but not desacyl-ghrelin, were significantly reduced by GO-CoA-Tat versus D4-Tat ("D4" disclosed as SEQ ID NO: 2) control, with $IC_{50}$'s in the 1-2 µM range.

Figure 7:
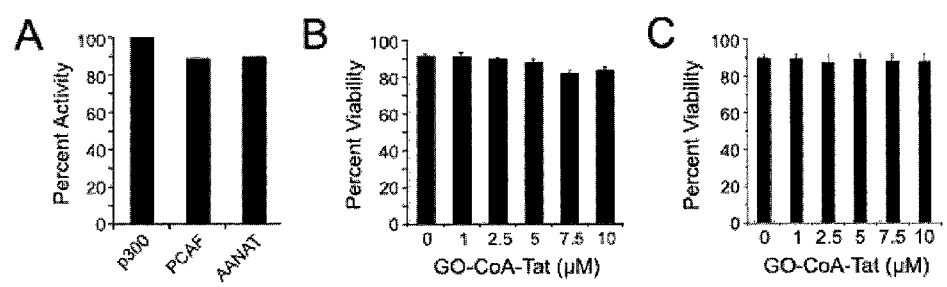
FIGS. 7A-7C: Assay for non-specific inhibition and toxicity of GOCoA-Tat. (A) Percent activity in the presence of 10 µM of GO-CoA-Tat in p300, PCAF and AANAT. (B) Viability of HepG2 cells and (C) HEL cells after 24 hr incubation with varying concentrations of GO-CoA-Tat.

GO-CoA-Tat appears to be a selective antagonist for GOAT because, at 10 µM, it showed less than 15% inhibition of three other acetyl-CoA utilizing enzymes in vitro, including p300 HAT, PCAF HAT, and serotonin N-acetyltransferase (FIG. 7). Moreover, 10 µM GO-CoA-Tat appears nontoxic to HEL cell and HEPG2 cell viability (FIG. 7). Furthermore, GO-CoA-Tat is likely to be acting as a bona fide bisubstrate analog in antagonizing GOAT activity (FIG. 1G). The fact that inclusion of the Tat sequence, or other moiety that aids in cell entry, increases inhibitory activity suggests that cell penetration is involved, and the compound is not acting on a cell surface receptor.

In one aspect of the invention, GO-CoA-Tat is administered, for example, intraperitoneally, to enhance insulin response to a glucose load and lead to a relative weight reduction in a mammal, e.g., in mice fed a high fat diet. Quantitative MR spectroscopy has established that GO-CoA-Tat treatment leads to a selective reduction in fat versus lean mass. Thus, GOAT can be targeted in treatment of obesity and glucose intolerance, and GO-CoA-Tat provides an effective GOAT inhibitor.

Compositions

In some embodiments, the invention provides compositions comprising a compound of formula I and a pharmaceutically acceptable excipient. As used herein, "pharmaceutically acceptable" encompasses those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In some embodiments, the term "pharmaceutically acceptable" means approved by a regulatory agency of the Federal or a state government or listed in the U.S. Pharmacopoeia or other generally recognized international pharmacopoeia for use in animals, and more particularly in humans. As used herein, "excipient" refers to a substance that is used in the formulation of pharmaceutical compositions, and, by itself, may be without therapeutic value. Various excipients can be used in the invention, including those described in Remington: The Science and Practice of Pharmacy, $21^{st}$ Ed. (2006), which is incorporated by reference. Excipients include, but are not limited to, antioxidants, anti-bacterial agents that prevent the decay of the formulation itself (as opposed to those exhibiting a therapeutic effect), preservatives, chelating agents, buffering agents, agents for adjusting toxicity, colorings, flavorings and diluting agents, emulsifying and suspending agents, and other substances with pharmaceutical applications.

The compositions of the invention can be administered in conjunction with other forms of obesity treatment, such as diet and exercise or bariatric surgery. In such combination therapies, the compositions of the invention can be administered before, simultaneously with, or after the other form of obesity treatment.

Pharmaceutical compositions for use in accordance with the present invention may be formulated in a conventional manner using one or more physiologically acceptable carriers comprising excipients and auxiliaries, which facilitate processing of the active ingredients into preparations which, can be used pharmaceutically. Proper formulation is dependent upon the route of administration chosen.

Suitable routes of administration may, include, for example, oral, rectal, transmucosal, especially transnasal, topical, intestinal or parenteral delivery, including intramuscular, subcutaneous and intramedullary injections as well as intrathecal, direct intraventricular, intravenous, intraperitoneal, intranasal, or intraocular injections. The pharmaceutical composition may be administered locally or systemically. For example, the composition can be administered locally via injection of the preparation directly into a specific region of a patient's body.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use. The active ingredient may also be subjected to PEGylation according to methods known in the art.

The preparations of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount is an amount of one or more active ingredients effective to prevent, alleviate or ameliorate symptoms of disease or prolong the survival of the subject being treated.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Methods of Preparing

In another aspect, the invention provides methods of preparing the compounds of Formula I. In some embodiments, the methods comprise the steps of providing a ghrelin peptide sequence comprising from 3 to 15 N-terminal amino acid residues, wherein the serine residue at the 3 position is replaced with alloc-protected 1,2-diaminopropionic acid and wherein a Tat sequence is bound to one end of the peptide sequence; combining the ghrelin peptide sequence with $Pd(PPh_3)_4$ palladium reagent, n-bromo octanoic anhydride and Reagent K in one or more reaction vessels to obtain a bromo-octanoylated intermediate; and combining the bromo-octanoylated intermediate with coenzyme A.

The Tat can be, for example, bound to one end of the R sequence of formula I. For example, if R is a peptide sequence, Tat can be attached to the C-terminal end of the peptide sequence. In some embodiments, Tat is attached through a linking moiety, such as, for example, an aminohexanoyl linker, though any linking moiety that does not interfere with the proper functioning of the GO-CoA-Tat is within the scope of the present invention.

"Reagent K" refers to a standard mixture of trifluoroacetic acid, water, thioanisole, phenol and ethanedithiol. It is used to deblock protected amino acids and cleave them from resin.

Synthesis of GO-CoA-Tat (e.g., Compound 1 as listed in FIG. 1C), can be performed using, for example, a solid phase strategy (FIG. 1B). A set of related compounds (Compounds 2-7, FIG. 1C) with different peptide lengths and individual deletion of CoA, octyl, and Tat, respectively, can also be synthesized (FIG. 1C) and used according to the present invention.

Methods of Prevention and Treatment

In another aspect, the invention provides methods of preventing and/or treating various diseases, disorders or conditions using a composition comprising therapeutically effective amount of a compound of Formula I.

"Treat" refers to curing, reversing, attenuating, alleviating, minimizing, suppressing or halting at least one of the symptoms or deleterious effects of the diseases, disorders or conditions described herein. "Treat" refers to both therapeutic treatment in a subject with the disease, disorder or condition. "Prevention" refers to prophylactic or preventative measures in a subject who has not developed signs or symptoms of the disorder. "Treat" encompasses, for example, alleviation of symptoms; diminishment of the extent of the condition, disorder or disease; stabilization (i.e., not worsening) of the state of the condition, disorder or disease; slowing of the condition, disorder or disease progression; amelioration of the condition, disorder or disease state; remission, whether partial or total; or enhancement or improvement of the condition, disorder or disease. Those in need of treatment include those already with the disorder. Those in need of prevention or prophylaxis include those in which the disorder can be prevented. Hence, the patient to be administered the compounds disclosed herein may have been diagnosed as having the disorder or may be predisposed or susceptible to the disorder. "Treatment" includes eliciting a measurable response, preferably a clinically significant response, without excessive levels of side effects. "Treatment" also includes prolonging survival as compared to expected survival if not receiving treatment.

The subject according to the present invention is a mammal, such as a human, that is diagnosed with one of the diseases, disorders or conditions described herein, or alternatively is predisposed to at least one type of the diseases, disorders or conditions described herein. The compositions of the present invention can be administered to any mammal in need of the composition that can experience the beneficial effects of the compounds of the invention. Any such mammal is considered a "subject." Such subjects include humans and non-humans, such as humans, domestic and farm animals, and zoo, sports, or pet animals, such as dogs, horses, cats, cows, etc. The subject can be a man or a woman.

The amount of active agent required to constitute a therapeutically effective amount will vary based on a number of factors, including the severity of the disorder to be treated; the identity, age, body weight, general health, gender, diet and chemical make-up of the patient; the type and degree of the cellular response to be achieved; the specific agents or composition employed, and its activity; the time of administration, route of administration, and rate of excretion of the agent; the duration of the treatment; drugs used in combination or coincidental with the specific agent; and similar factors well known in the medical arts. In general, a therapeutically effective amount is an amount that produces a measurable alleviation of one or more symptoms associated with a disease or disorder.

For example, a therapeutically effective amount for treating or preventing obesity can be up to or at least about 1 mg/kg, 1.5 mg/kg, 2 mg/kg, 2.5 mg/kg, 3 mg/kg, 5 mg/kg, 7.5 mg/kg, 10 mg/kg, 15 mg/kg, 20 mg/kg, 25 mg/kg, 30 mg/kg or more of the active agent per day. For a 70 kg person, a therapeutically effective dose can be up to or at least about 50 mg, 60 mg, 70 mg, 80 mg, 90 mg, 100 mg, 120 mg, 140 mg, 160 mg, 180 mg, 200 mg, 210 mg, 250 mg, 300 mg, 350 mg, 400 mg, 450 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg or more of the active agent per day. As used herein, "about" may refer to a range from 10% below the referenced number to 10% above the referenced number. For example, "about 50" may mean from 45 to 55.

For example, it is well within the skill of the art to start doses of the agents at levels lower than those required to achieve the desired therapeutic effect and to gradually increase the dosages until the desired effect is achieved. The therapeutically effective amount of the active agent under these circumstances may readily be determined by a practitioner using animal and clinical trials and medical observations.

In some embodiments, the invention provides methods of treating or preventing obesity. The methods can comprise administering to a subject a composition comprising a therapeutically effective amount of the compound of Formula I.

According to the invention, administering the composition can bring about, for example, a greater loss of fat mass than lean mass in the subject. It can also bring about, for example, an increase in the ratio of ghrelin to acyl-ghrelin in the subject.

In some embodiments, the invention provides methods of treating or preventing diabetes, for example type II diabetes. The methods can comprise administering to a subject a composition comprising a therapeutically effective amount of the compound of Formula I. Administering the composition can bring about, for example, an increased production of insulin in the subject. It can also bring about, for example, an increased responsiveness to a glucose challenge in the subject, and/or a reduction in uncoupling-protein 2 (UCP-2) mRNA levels in the subject.

The therapeutically effective amount of the compounds of Formula I for treating or preventing diabetes can be determined by one of ordinary skill in the art, though it can be, for example, similar to that described above for obesity.

For example, a therapeutically effective amount for treating or preventing diabetes can be up to or at least about 1 mg/kg, 1.5 mg/kg, 2 mg/kg, 2.5 mg/kg, 3 mg/kg, 5 mg/kg, 7.5 mg/kg, 10 mg/kg, 15 mg/kg, 20 mg/kg, 25 mg/kg, 30 mg/kg or more of the active agent per day. For a 70 kg person, a therapeutically effective dose can be up to or at least about 50 mg, 60 mg, 70 mg, 80 mg, 90 mg, 100 mg, 120 mg, 140 mg, 160 mg, 180 mg, 200 mg, 210 mg, 250 mg, 300 mg, 350 mg, 400 mg, 450 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg or more of the active agent per day.

Without wishing to be bound by any particular theory, GOAT inhibition appears to treat diabetes by decreasing levels of uncoupling protein-2 (UCP-2) in pancreatic islet cells. That GOAT inhibition modulates UCP2 levels so dramatically further substantiates the connection of acyl-ghrelin to obesity and type 2 diabetes. Acyl ghrelin induces feeding behavior by causing an increase in UCP2 levels in arcuate nucleus neurons that co-express neuropeptide Y and agouti-related protein. UCP2 can be markedly upregulated in islets of ob/ob mice, a model of obesity-induced diabetes. Importantly, ob/ob mice lacking UCP2 exhibit restored first-phase insulin secretion, increased serum insulin levels, and greatly decreased levels of glycemia.

Furthermore, a human UCP2 polymorphism, A55V, is associated with obesity and markedly increased insulin and leptin concentrations. Furthermore, type 2 diabetic patients homozygous for the −866 A UCP2 promoter polymorphism have elevated UCP2 expression and require a higher frequency of insulin treatment. These patients also have significantly lower glucose-induced insulin secretion (GIIS). Moreover, the islets isolated from −866 A/A donors have significantly lower GIIS than those isolated from −866 G/A heterozygous and G/G homozygous individuals.

In some embodiments, the invention provides methods of treating mBOAT-associated diseases. For example, the methods can comprise administering to a subject a composition comprising a therapeutically effective amount of the compound of Formula I, thereby treating the mBOAT-associated disease.

An "mBOAT associated disease" is a disease characterized by dysregulation of a pathway in which an mBOAT peptide is involved. There are at least sixteen mBOAT genes. For example, a gene product known as "porcupine," which has structural similarities to mBOAT proteins, is integral to Wnt signaling, a process associated with cancer. Wnt requires acyl modification by the porcupine acyltransferase enzyme. Wnt signaling may contribute to many cancers and could be blocked by porcupine inhibitors. mBOAT associated diseases include various forms of lipid metabolism dysregulation. Altered lipid metabolism can contribute to cancer, and blocking mBOATs can provide cancer treatments.

In some embodiments, the invention provides methods of treating or preventing disorders associated with gastric motility dysregulation, such as, for example, irritable bowel syndrome. Ghrelin administration increases gastric emptying and is associated with decreased gastroparesis. Therefore, administration of GO-CoA-TAT can be used to inhibit gastric motility via its inhibition of GOAT and the concomitant decrease in acyl-ghrelin levels, exerting a palliative effect in patients with irritable bowel syndrome and other disorders associated with gastric motility dysregulation, as would be understood by a person of ordinary skill in the art.

Kits

In another aspect, the invention provides kits. In some embodiments, the kits comprise a composition comprising at least one dose of a therapeutically effective amount of the compound of Formula I.

The kits can further comprise at least one dose of an additional weight loss treatment. Examples of such additional treatments include, for example, antibodies against acyl-ghrelin as well as antagonists to GHSR.

Directly targeting the biosynthesis of the active acyl-ghrelin hormone offers several advantages over receptor antagonists. First, these enzyme inhibitors do not need to cross the blood-brain barrier, in contrast to acyl-ghrelin receptor blockers, for which many of the key sites of action are in the brain. Second, the effect of an enzyme inhibitor is likely to be more global in scope. For example, there may be classes of acyl-ghrelin receptors other than GHSR that have not yet been identified, and which would presumably not be affected by receptor antagonists targeting known receptors. However, the activities of these as-yet unknown receptors would of course be impacted by decreased hormone levels. Third, receptor blockers have the disadvantage that animals may have feedback mechanisms that would drive higher acyl-ghrelin formation in response to receptor blockade, which might overwhelm receptor blockers. However, such a feedback mechanism would be effectively counteracted by an enzyme inhibitor, which targets the biosynthetic pathway and thus prevents the feedback mechanism from increasing acyl-ghrelin levels. Fourth, because the GOAT enzyme acts catalytically, a given dose of GOAT inhibitor is likely to be proportionately more effective than a similar dose of an acyl-ghrelin receptor blocker, which is only capable of more or less one-to-one effectiveness. Fifth, there is some suggestion that the ratio of ghrelin to acyl-ghrelin is the important factor in modulating weight gain, with relatively higher ghrelin concentrations favoring weight loss, and this is precisely the effect achieved by a GOAT inhibitor. In summary, this invention sets forth a novel approach for the pharmacologic management of weight and glucose control.

Additional objects, advantages, and novel features of the present invention will become apparent to one of ordinary skill in the art upon consideration of the following examples, which are not intended to limit the scope of the invention in any way.

EXAMPLES

Example 1

Effect of GO-CoA-Tat on Acyl-Ghrelin Production in Three Cell Lines

Figure 5:
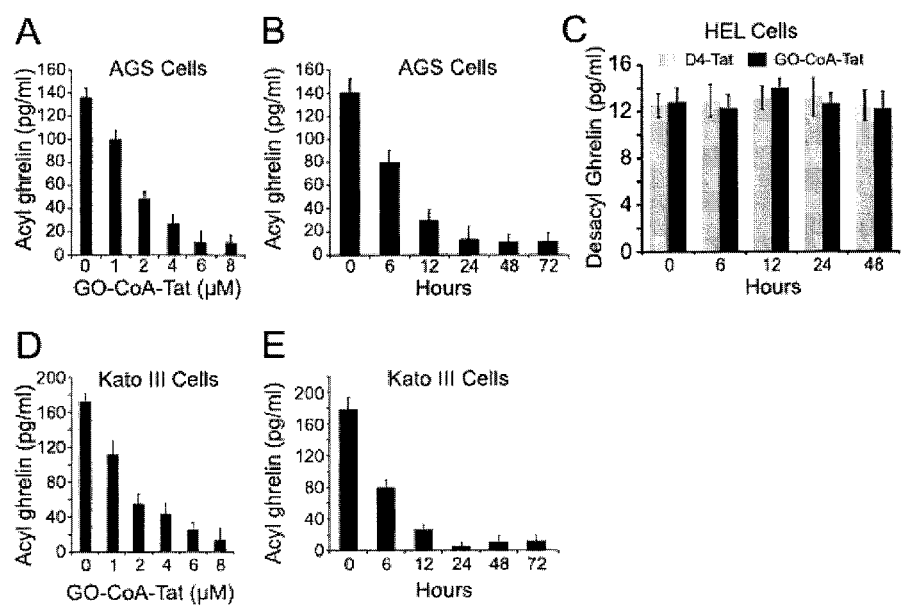
FIG. 5A-5E: GO-CoA-Tat lowers acyl- but not desacyl-ghrelin levels in AGS and Kato III cells. (A) Dose-response inhibition of acyl-ghrelin (pg/ml) in AGS cell lysate (2.5×10$^6$ cells) after 24 hr incubation with various concentrations of GO-CoA-Tat. (B) Temporal inhibition of 6 µM GO-CoA-Tat in AGS cell lysate (2.5×10$^6$ cells). (C) Dose-response of desacyl ghrelin (pg/ml) in HEL cell lysate (2.5×10$^6$ cells) after 24 hr incubation with various concentrations of GO-CoA-Tat and D4-Tat ("D4" disclosed as SEQ ID NO: 2). (D) Dose-response inhibition after 24 hr incubation and (E) temporal inhibition of 6 µM GO-CoA-Tat in Kato III cells. Figures disclose "D4" disclosed as SEQ ID NO: 2.
Figure 6:
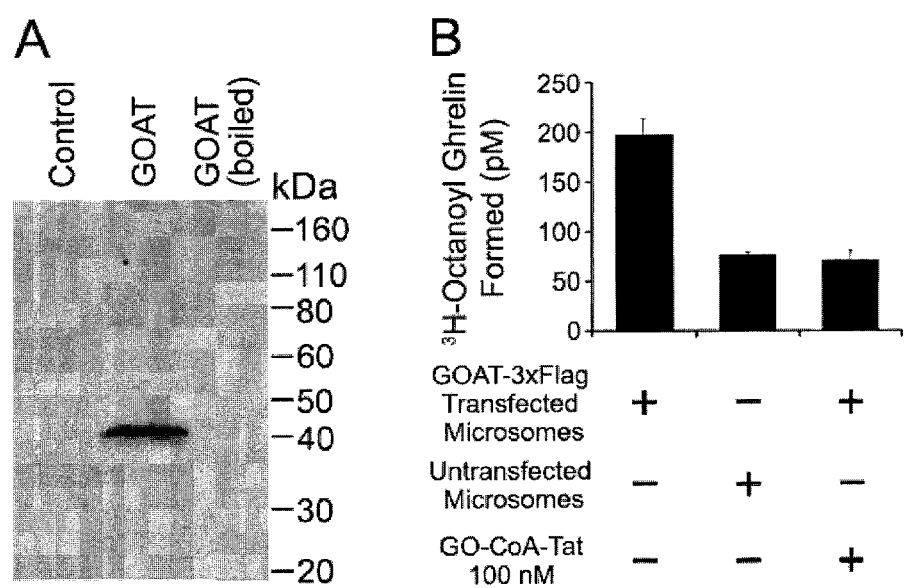
FIGS. 6A-6B: Establishment of an in vitro assay for GOAT. GOAT was present in microsomes isolated from HEK293T GnTI(−) cells. HEK293T GnTI(−) cells were transfected with GOAT-3× Flag or empty vector (Control) and microsomes were prepared as described in the Examples. (A) Immunoblot analysis with 10 µg/mL monoclonal anti-FLAG antibody of microsomes (50 µg of protein) from transfected and untransfected cells. GOAT-transfected microsomes incubated at 50° C. in SDS-PAGE loading dye for 5 min, but not those boiled at 100° C. for equal time, reveal a band at 42 kDa, indicating the presence of GOAT. (B) GOAT activity is present in microsomes from transfected but not untransfected cells and is completely inhibited by GO-CoA-Tat at 100 nM.

At the outset of this work, an in vitro GOAT assay had not yet been developed so we investigated the effects of GO-CoA-Tat on acyl-ghrelin production in three cell types including HEL human erythroleukemia cells (FIG. 1 D-E), Kato III human gastric cells (FIG. 5) and AGS human gastric epithelial cells (FIG. 5) (all three cell lines obtained from ATCC, Manassas, Va.). We employed D4-Tat ("D4" disclosed as SEQ ID NO: 2) (tetra-aspartate, to simulate the negative CoA charge, similarly linked to the Tat peptide) as a control. In each of the cell lines, levels of acyl-ghrelin, but not desacyl-ghrelin, were significantly reduced by GO-CoA-Tat vs. D4-Tat ("D4" disclosed as SEQ ID NO: 2) control with IC50's in the 1-2 µM range. Interestingly, maximal inhibition was achieved only after 24 h of exposure to compound; the slow kinetics might result from either atypical enzymatic characteristics or preformed acyl-ghrelin stores. To further investigate this delay, we tested GO-CoA-Tat in vitro with recombinant microsomal GOAT (FIGS. 1 F and 6) using a radioactive assay (14). Complete GOAT inhibition was achieved with 100 nM GO-CoA-Tat within 5 min, suggesting that the slow apparent reduction of cellular acyl-ghrelin levels may reflect a significant preexisting intracellular reservoir.

GO-CoA-Tat appears to be a selective GOAT antagonist since at 10 µM, it showed less than 15% inhibition of three acetyl-CoA utilizing enzymes in vitro including p300 HAT, PCAF HAT, and serotonin N-acetyltransferase (FIG. 7). Moreover, 10 µM GO-CoA-Tat appears non-toxic to HEL cell and HEPG2 cell (ATCC, Manassas, Va.) viability (FIG. 7). A broader analysis of GO-CoA-Tat and analogs suggests optimum results are achieved using at least 10 ghrelin residues, as well as the CoA, octanoyl, and Tat components, for potent cellular inhibition of acyl-ghrelin production. These results imply that GO-CoA-Tat is likely acting as a bona fide bisubstrate analog in antagonizing GOAT activity (FIG. 1G). Furthermore, the fact that best results are achieved by inclusion of a moiety that assists in cell penetration, such as the Tat sequence, suggests that cell penetration is involved, and the compound is not acting on a cell surface receptor.

Example 2

Effect of GO-CoA-Tat Administration on Acyl-Ghrelin Production in Mice

Figure 2:
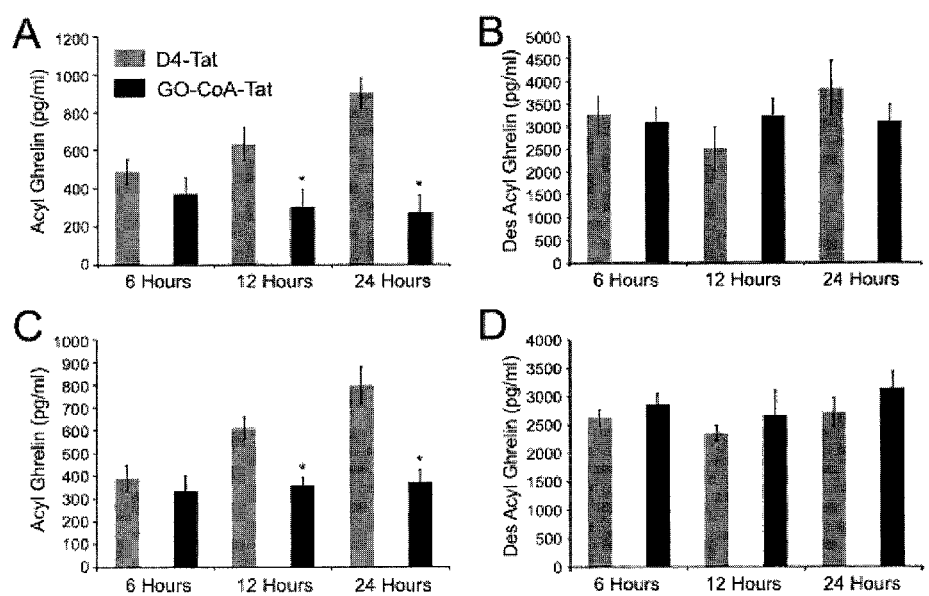
FIGS. 2A-2D: GO-CoA-Tat lowers circulating acyl- but not desacyl-ghrelin levels in mice. (A) Mice treated with 29 mg/kg GO-CoA-Tat (n=3) experienced a statistically significant reduction in acyl-ghrelin as compared with those treated with D4-Tat ("D4" disclosed as SEQ ID NO: 2) control. (B) Desacyl-ghrelin levels exhibited no statistically significant difference in mice treated with GO-CoA-Tat versus control mice treated with the molar equivalent of D4-Tat ("D4" disclosed as SEQ ID NO: 2) (n=3) after 12 and 24 hours. Similar results with lesser inhibition were seen with 15 mg/kg GO-CoA-Tat (C, D). Figures disclose "D4" disclosed as SEQ ID NO: 2.

We next examined whether GO-CoA-Tat blocks acyl-ghrelin production in normal mice. We tested two intraperitoneal (IP) GO-CoA-Tat doses, 15 mg/kg and 29 mg/kg, in mice fasted for 6 h prior to compound administration. These doses are predicted to achieve a maximal concentration of approximately 4 and 8 µM, respectively, assuming a volume of distribution equal to animal weight. Treatment with GO-CoA-Tat, but not D4-Tat ("D4" disclosed as SEQ ID NO: 2) control, led to a dose-dependent blockade of serum acyl-ghrelin (FIG. 2), with a maximum of 70% inhibition at 24 h with a 29 mg/kg dose, as was observed in cell culture (FIG. 2). Again there was no significant effect on serum levels of des-acyl ghrelin, although there was a slight trend toward an increase. These results demonstrate that GO-CoA-Tat selectively targets acyl-ghrelin production in vivo.

Example 3

Effect of GO-CoA-Tat Administration on Weight Gain in Mice

Figure 3:
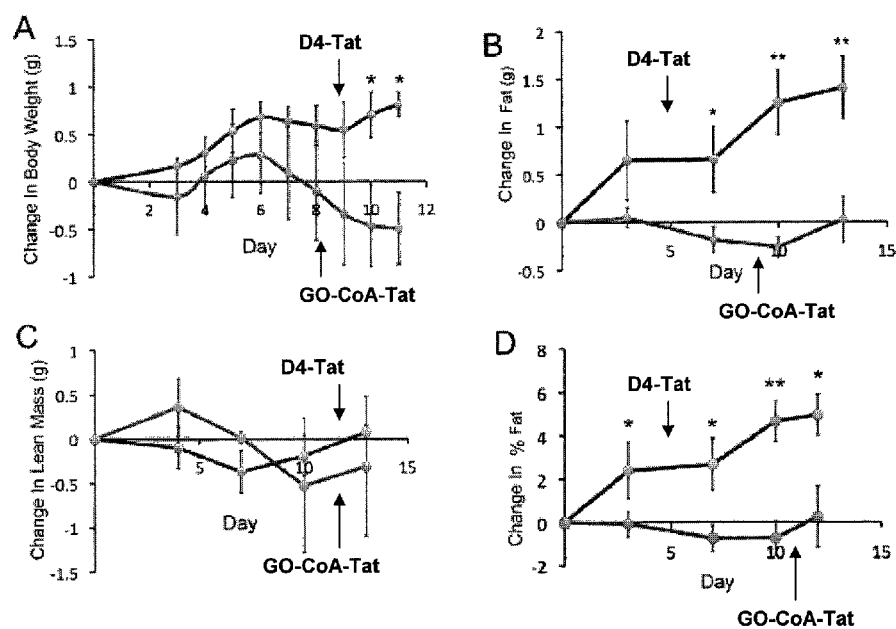
FIGS. 3A-3D: Effects of GO-CoA-Tat on body weight and composition in mice. Mice treated with 29 mg/kg GO-CoA-Tat (n=3) experienced (A) a statistically significant decrease in body weight (* <0.05, with three day standard error), (B) a statistically significant decrease in grams of body fat, (C) no statistically significant difference in lean mass, and (D) a statistically significant decrease in percent body fat (* <0.05, ** <0.005) versus mice treated with D4-Tat ("D4" disclosed as SEQ ID NO: 2) (n=3). Figures disclose "D4" disclosed as SEQ ID NO: 2.
Figure 8:
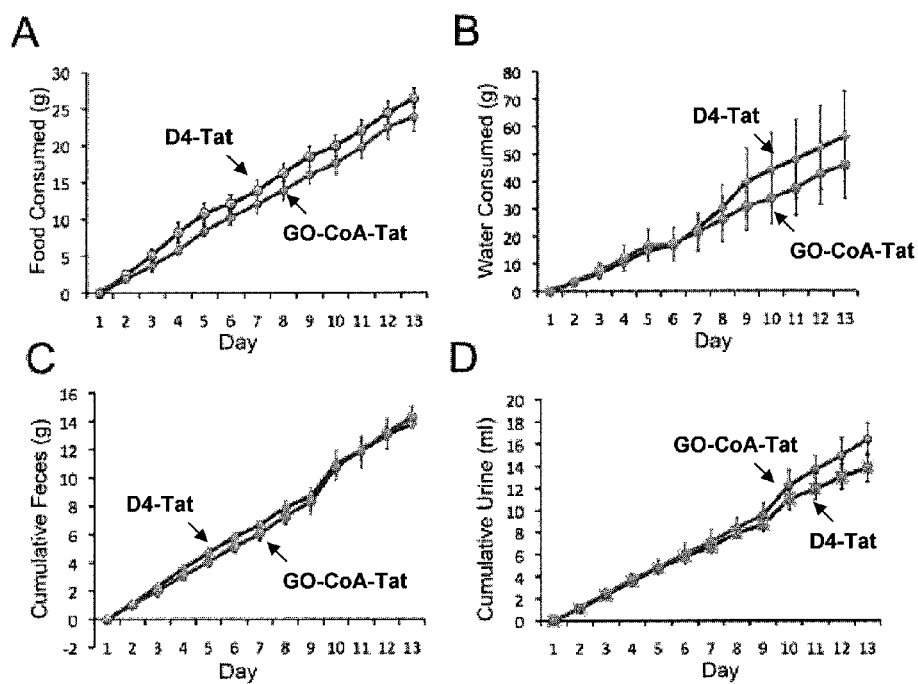
FIGS. 8A-8D: Effects of GO-CoA-Tat on intake and excretion. (A) Mice treated with 29 mg/kg GO-CoA-Tat (n=3) and D4-Tat ("D4" disclosed as SEQ ID NO: 2) (n=3) did not have statistically significant difference in cumulative food and (B) water consumption. (C) The cumulative feces and (D) urine production of these mice also were not different to a statistically significant degree. Figures disclose "D4" disclosed as SEQ ID NO: 2.

We next examined the effect of GO-CoA-Tat on weight gain by feeding normal mice a high fat diet over a 12 d period. These mice were treated every 24 h with GO-CoA-Tat (29 mg/kg IP) and studied in metabolic cages allowing daily monitoring of intake and output as well as body mass. In addition, the mice were subjected every 3 d to quantitative magnetic resonance (QMR) spectroscopy to evaluate the animals' fat and lean mass (15). These experiments showed that mice treated with GO-CoA-Tat exhibited a statistically significant reduced weight relative to those treated with D4-Tat ("D4" disclosed as SEQ ID NO: 2) (FIG. 3A). Moreover, the QMR measurements showed that, relative to controls, the GO-CoA-Tat treated animals displayed about a 5% relative reduction in fat mass, but not lean mass, which persisted after day 6 (FIG. 3B-D). There were no statistically significant differences in food and water intake or fecal and urine output (FIG. 8), but there was relatively wide variation in these values in our modest sample size, so a contribution from reduced intake cannot be ruled out. Prior genetic studies suggest that loss of ghrelin can affect weight by influencing appetite as well as metabolic rate (2-8).

To investigate the potential for GO-CoA-Tat induced generalized toxicity or organ damage as a source of weight loss, we assessed the blood chemistries and blood cell counts in the 12 day GO-CoA-Tat treated animals. These analyses showed no evidence of liver, renal, pancreas, or bone marrow toxicities that could account for weight loss (FIG. 9). Interestingly, in these blood measurements, GO-CoA-Tat induced small but significant increases in HDL as well as triglycerides. In a separate study, the total fecal fat over the three day period as determined by QMR demonstrated no statistical significance between GO-CoA-Tat (4.97+/−0.10 g) and D4-Tat ("D4" disclosed as SEQ ID NO: 2) (5.01+/−0.07 g) treated mice, suggesting that GOAT inhibition does not affect intestinal fat absorption. Together, these data suggest that GO-CoA-Tat causes weight loss by lowering acyl-ghrelin.

Example 4

Effect of GO-CoA-Tat on Insulin Response to Glucose Challenge

Figure 4:
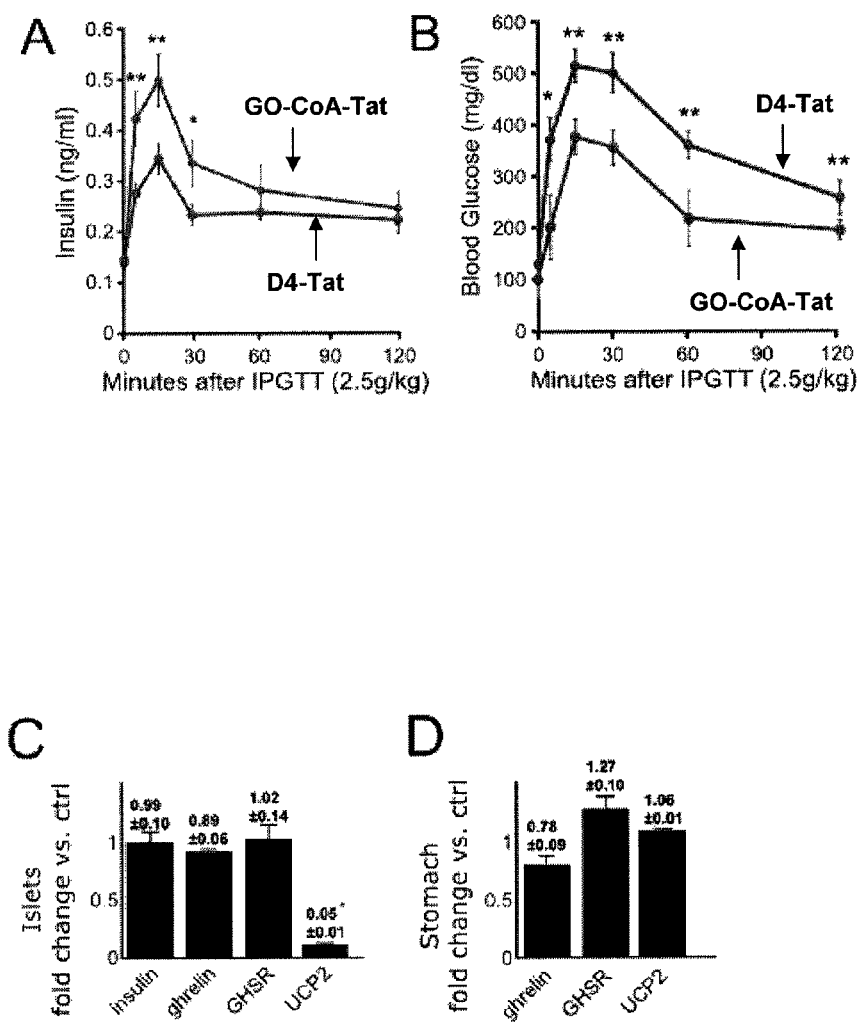
FIGS. 4A-4D: GO-CoA-Tat increases insulin, decreases glucose levels, and down-regulates UCP2 mRNA. (A) Mice treated with 29 mg/kg GO-CoA-Tat (n=4) experienced a statistically significant increase in insulin secretion and (B) a statistically significant decrease in blood glucose as compared to mice treated with D4-Tat ("D4" disclosed as SEQ ID NO: 2) (n=6) when compound was administered 24 hrs prior to oral glucose challenge (1 g/kg) and blood glucose and insulin values were measured every thirty minutes after intraperitoneal glucose tolerance test (IPGTT) (2.5 g/kg). (C) QRT-PCR of islets and (D) gastric fundus isolated from mice treated with inhibitor 24 hrs prior to isolation; isolation of mRNA expression, measured relative to control (n=3). Figures disclose "D4" disclosed as SEQ ID NO: 2.
Figure 10:
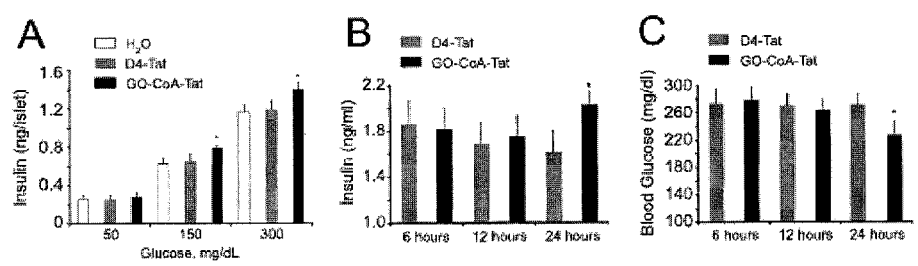
FIGS. 10A-10C: Effect of GO-CoA-Tat on insulin and glucose in islets and mice. (A) Incubation with 5 µM compound GO-CoA-Tat causes a statistically significant increase in insulin production when human islets are incubated in 150 mg/dl and 300 mg/dl glucose (n=9). (B) Mice treated with 15 mg/kg GO-CoA-Tat (n=6) experienced a statistically significant increase in insulin secretion and (C) a statistically significant decrease in blood glucose. Figures disclose "D4" disclosed as SEQ ID NO: 2.

To investigate the effect of GO-CoA-Tat on insulin response to a glucose challenge, we pre-treated human islet cells with GO-CoA-Tat for up to 24 h and showed that these cells displayed a statistically significant increase in insulin response to a glucose challenge when exposed to 24 h GO-CoA-Tat (FIG. 10). These results suggest that acylated ghrelin plays a direct role in blunting insulin response. To investigate this in vivo, we studied mice that received an oral glucose challenge after pre-treatment with GO-CoA-Tat. Consistent with the islet cell studies, animals given 15 mg/kg GO-CoA-Tat 24 h prior to the oral glucose challenge (1 g/kg) showed a statistically significant increase in insulin response (FIG. 10). This result was even more substantial in mice receiving 29 mg/kg GO-CoA-Tat with an intraperitoneal glucose challenge of 2.5 g/kg (FIG. 4A). This increased insulin response was accompanied by a statistically significant reduction in glucose, suggesting a functionally meaningful effect (FIG. 4B).

To further investigate the connection between GOAT inhibition and insulin regulation, we studied pancreatic islets isolated from mice treated with GO-CoA-TAT. The insulin-producing β-cells stained positive for GHSR and islets exhibited a small population of ghrelin expressing cells, which are distinct from β-cells, demonstrating that insulin and the ghrelin receptor are likely produced in separate cells. QRT-PCR of islets isolated from mice treated with GO-CoA-Tat demonstrated a 20-fold reduction in UCP2 mRNA levels as compared to D4-tat ("D4" disclosed as SEQ ID NO: 2) treated mice (FIG. 4C) but no change in levels of insulin, ghrelin, or GHSR. By comparison, QRT-PCR showed non-statistically significant effects on UCP2 in the gastric fundus (FIG. 4D). Taken together, these data point to a tissue-specific role for GOAT inhibition in suppressing UCP2 levels and enhancing insulin release in response to glucose.

That GOAT inhibition modulates UCP2 levels so dramatically further substantiates the connection of acyl-ghrelin to obesity and type 2 diabetes (19-21). Acyl-ghrelin induced feeding behavior can be controlled by increasing UCP2 levels in arcuate nucleus neurons that co-express neuropeptide Y and agouti-related protein (21). UCP2 is markedly upregulated in islets of ob/ob mice, a model of obesity-induced diabetes. Importantly, ob/ob mice lacking UCP2 exhibit restored first-phase insulin secretion, increased serum insulin levels, and greatly decreased levels of glycemia (19). Furthermore, a human UCP2 polymorphism, A55V, is associated with obesity and markedly increased insulin and leptin concentrations (22). Further, Type 2 diabetic patients homozygous for the −866 A UCP2 promoter polymorphism have elevated UCP2 expression and require a higher frequency of insulin treatment. These patients also have significantly lower glucose-induced insulin secretion (GIIS) (23). Moreover, the islets isolated from −866 A/A donors have significantly lower GIIS than those isolated from −866 G/A heterozygous and G/G homozygous individuals (24).

Example 5

Chemical Synthesis (Compounds 1-7, D4-Tat ("D4" Disclosed as SEQ ID NO: 2), Ghrelin-27-Biotin)

All reagents for chemical synthesis were purchased from Aldrich or Acros Organics. All commercially available reagents were used as purchased without further purification. Preparative HPLC isolation of bisubstrate analog inhibitors, peptides, and control compounds was performed on a reverse-phase C-18 column (25×2.14 cm, Microsorb™-100, Rainin), eluted with a gradient of water (0.05% trifluoroacetic acid (TFA), mobile phase A) and acetonitrile (0.05% TFA, mobile phase B). Ghrelin-27-biotin (GSSFLSPE-HQRVQQRKESKKPPAKLQPK(Biotin)G) (SEQ ID NO: 4) and D4-Tat ("D4" disclosed as SEQ ID NO: 2) were prepared using the Fmoc strategy. Synthesis of GO-CoA-Tat and related derivatives was analogous to previously described methods (33, 34) beginning with ghrelin and using the Fmoc strategy. Variable lengths of ghrelin peptide (3 to 15 C-terminal sequences) were employed and Ser3 in ghrelin was replaced with Alloc (allyloxycarbonyl) protected-1,2-diaminopropionic acid. Orthogonal deprotection of Alloc using tetrakis(triphenylphosphine)palladium(0) in $CHCl_3$:AcOH: N-methylmorpholine(37:2:1) to give the free amino group was carried out followed by reaction with racemic α-bromo octanoic anhydride (octanoic anhydride and bromoacetic anhydride for compounds 5 and 6, respectively (see FIG. 1C). Conjugation with coenzyme A was performed by reacting the α-bromo-amide with CoASH. To a stirred solution of bromo-amide peptide (concentration 2-10 mM in ddH2O) was added dropwise a solution of CoASH (2.0-3.0 equivalent) in a 1.0 M aqueous buffer solution of triethylammonium bicarbonate (pH 8.0) at room temperature. After 48-72 hrs, the mixture was lyophilized overnight, and the residue was subjected to preparative HPLC to isolate the desired products. The HPLC column was eluted with a gradient of water (0.05% TFA, mobile phase A) and acetonitrile (0.05% TFA, mobile phase B) (0 min, 5% B; 5-65 min, linear increase to 60% B; 10 mL/min), and was monitored at 214 nm. The collected fractions were concentrated under reduced pressure and lyophilized to give the final products as white solids. Their matrix-assisted laser desorption/ionization (MALDI) and electrospray (ES)-mass spectrometry data were consistent with the calculated values and the final concentrations of the compounds in aqueous solution for assay were determined by amino acid analysis.

Example 6

Cell Culture, Cell Lysate Preparation and EIA Measurements

HEL cells and AGS cells (ATCC, Manassas Va.) were grown in RPMI 1640 medium (Sigma) supplemented with 10% inactivated fetal bovine serum, 100 IU/ml streptomycin-penicillin, and 4 mM glutamine and were routinely passaged twice a week. Kato III cells (ATCC, Manassas Va.) were grown in DMEM media supplemented with 10% inactivated fetal bovine serum, 100 IU/ml streptomycin-penicillin, and 4 mM glutamine and were routinely passaged twice a week. In some experiments HEL cells were treated with one of seven compounds to assess inhibition of acyl-ghrelin production. Cell lysate from all three cell types was prepared in RIPA buffer as follows. Cells ($7.5 \times 10^6$ cells) were centrifuged at 1000 rpm in a table-top centrifuge for 5 minutes. The cell pellet was then washed and to this 0.25 ml of ice-cold modified RIPA buffer containing was added and vigorously pipetted and vortexed and then allowed to sit for 10 minutes at 4° C. to thoroughly lyse cells. The lysate was then spun down at 2,000 rpm in a precooled centrifuge for 15 minutes. Immediately after centrifugation, the supernatant was stored at –80° C. To assess levels of acyl- and desacyl-ghrelin in cell lysates and serum and insulin levels in culture media and serum samples were analyzed on a commercially available double-antibody sandwich based Enzyme Immunometric Assay (Alpco Diagnostics).

Example 7

Molecular Cloning

GOAT was cloned by a two-stage nested RT-PCR scheme from mouse stomach. Total RNA was extracted from the proximal half of a mouse stomach, using a tissue homogenizer and an RNeasy® Kit (Qiagen). cDNA was prepared by reverse transcription with Invitrogen SuperScript™ II RT. 2 µl of cDNA was amplified with primers TTTA-CAAGGGCACCGCTTAG (SEQ ID NO: 5)/CAAG-GCATCTTCTGGCATTT (SEQ ID NO: 6). 1 µl of the reaction mixture was then further amplified with nested primers GCCACCATGGATTGGCTCCAGCTC (SEQ ID NO: 7)/GAGATGAAGGGCAGGGAAA (SEQ ID NO: 8). A band at ~1.3 kB was excised from the gel and ligated into pCR® 2.1-TOPO® (Invitrogen).

GOAT was amplified from this vector using primers designed for 5' blunt ligation and 3' EcoRI cleavage, then cloned into the paH vector, derived from pHLsec (Aricescu et al. Acta Cryst. (2006). D62, 1243-1250) using KpnI (blunted) and EcoRI. A 3× Flag® tag (Sigma) was added to the C-terminus using QuikChange® mutagenesis (Stratagene), replacing the manufacturer's protocol with the two-stage procedure developed by Wang and Malcolm (35).

Example 8

GOAT Transfection and Microsomal Isolation

GnTI-deficient HEK293T cells (Reeves et al., Proc Natl Acad Sci USA. 2002 Oct. 15; 99(21):13419-24) were grown in Freestyle 293T media (Invitrogen) supplemented with 2 mM L-glutamine and 1% FBS in an atmosphere containing 8% $CO_2$. On the day of transfection, 400 ml of cells were set up at a concentration of $2 \times 10^6$/ml. Cells were transfected with plasmids using Polyethylenimine "Max" high potency linear PEI (Polysciences) as described by Aricescu et al. (Acta Cryst. (2006). D62, 1243-1250). Briefly, 1 µg/ml of DNA was mixed with 3 µg/ml of transfection reagent in unsupplemented Hybridoma SFM medium (Invitrogen) equivalent to $\frac{1}{20}^{th}$ final culture volume, incubated for 20 min at room temperature, and added to the cells. Cells were harvested for experiments after 4 days and washed once with PBS.

Each pellet of HEK293T GnTI-cells was resuspended in 20 ml Buffer D (50 mM Tris-HCl, pH 7.4, 150 mM NaCl, 1 mM sodium-EGTA, 30 µg/ml phenylmethylsulfonyl fluoride, 3 µg/ml Pepstatin A, and a Complete Protease Inhibitor Cocktail Tablet, EDTA-free (Roche, 1 tab/40 ml buffer)). Cells were lysed using a dounce homogenizer (type B pestle, 30 strokes). Lysates were centrifuged at 2,135×g at 4° C. for 10 min, and the supernatant was transferred to a new tube and centrifuged again under the same conditions. The supernatant was then centrifuged at 100,000×g at 4° C. for 30 min and the supernatant discarded. The microsome pellet was resuspended in Tris-buffered saline (TBS) (50 mM Tris-HCl, pH 7.4, 150 mM NaCl) and insoluble material was removed by centrifuging at 1,000×g for 1 min. Aliquots were prepared for immunoblot analysis or flash-frozen in liquid nitrogen and stored at –80° C. until the time of assay. Protein concentrations were measured using the BCA assay (Thermo) supplemented with 0.5% Triton X-100.

Example 9

GOAT Acyltransferase Assay

The assay protocol was modified from Yang et al. (36). The assay mixture contained 50 mM HEPES, pH 7.0, 1 µM octanoyl-CoA (33 dpm/fMol, American Radiolabeled Chemicals), 10 µM Ghrelin27-Biotin, 50 µg microsome protein, and 50 µM palmitoyl-CoA (Avanti Polar Lipids). Reactions were initiated by the addition of membrane protein and incubated at 37° C. for 5 min. Where indicated, GO-CoA-Tat was pre-incubated for 5 min with the membrane protein.

Reactions were quenched by the addition of 850 µl of quench buffer (TBS+2% (w/v) SDS) pre-mixed with 150 µl Streptavidin Plus UltraLink Resin (Pierce) and incubated for 15 min on a rotating mixer. This mixture was transferred to a Poly-Prep® chromatography column (Bio-Rad) and washed with 30 ml wash buffer (TBS+0.1% SDS). The mixture was transferred to a 1.5 ml microcentrifuge tube containing 1 ml quench buffer, boiled at 98° C. for 5 min, and subjected to scintillation counting.

Example 10

Cell Viability Assay

The viability of the HEL cell line and the human immortalized hepatocyte cell line HepG2 (ATCC, Manassas, Va.) treated with the varying concentrations of GO-CoA-Tat was determined using a LIVE/DEAD viability assay kit (Molecular Probes). Rat bone marrow stromal cells (RBMSCs) were incubated with two probes, 2 µM calcein-AM (green color) for 30 min and 4 µM ethidium homodimer-1 (EtdD-1, bright red color) for 10 min, for intracellular esterase activity and plasma membrane integrity, respectively. Calcein-AM was excited using the 500 nm laser line, and the emitted fluorescence was detected through a 535 nm long-pass filter. EtdD-1 was excited using the 514 nm laser line, and the emitted fluorescence was detected through a 550 nm long-pass filter. Red fluorescent (EtdD-1) cells were counted as dead, and green fluorescent (Calcein-AM) were counted as viable. In cases of dual partial red and green staining, cells were counted as dead.

Example 11

Human Islet Experiments

Fresh human cadaveric islets were provided by the National Islet Cell Resource Center. Average purity and viability were 70% and 85%, respectively. For human islet experiments, islets were incubated in serum-free RPMI media with 5 µM GO-CoA-Tat for 24 hrs prior to a static incubation assay for thirty minutes in glucose-free RPMI media with 50, 150 and 300 mg/dl glucose added and the insulin secreted into the medium was assessed with ELISA (Alpco Diagnostics).

Example 12

Acetyltransferase Assays

The specificity of GO-CoA-Tat with the acetyltransferases p300, PCAF, and AANAT was measured using an α-ketoglutarate dehydrogenase (α-KGDH) coupled spectrophotometric assay (37). Recombinant acetyltransferase domains and histone tail peptides were prepared as described previously (38-40). The production of CoASH by the acetyltransferase is coupled to the formation of NADH, which is monitored at 340 nm ($\epsilon_{340}$=6230 M$^{-1}$ cm$^{-1}$) in a Beckman DU-640 spectrophotometer. All reactions contain 200 µM thiamine pyrophosphate, 5 mM $MgCl_2$, 1 mM DTT, 50 µg/mL BSA, 200 µM NAD, 2.4 mM α-ketoglutarate, 10 µM GO-CoA-Tat, and 50 µM acetyl-CoA. Reactions with p300 were performed in 100 mM HEPES, pH 7.9, and contain 0.1 units α-KGDH and 200 µM H4-15, a 15-mer peptide substrate based on the sequence of the histone H4 tail. p300 reactions are incubated at 30° C. prior to initiation with addition of 100 nM p300 and take place at 30° C. Reactions with PCAF are performed in 100 mM HEPES, pH 7.9, and contain 0.037 units α-KGDH and 100 µM H3-20, a 20-mer peptide substrate based on the sequence of the histone H3 tail. PCAF reactions are incubated at 30° C. for 10 minutes prior to initiation with addition of 100 nM PCAF and take place at 30° C. Reactions with AANAT are performed in 100 mM $NH_4OAc$, pH 6.8, and contain 0.1 units α-KGDH and 200 µM tryptamine. AANAT reactions are incubated at 25° C. for 10 minutes prior to initiation with addition of 10.83 nM AANAT and take place at 25° C. All reactions are followed over the linear portion of the progress curve, which provides the initial velocity via linear regression.

Example 13

Murine Experiments

For all 24 hour experiments C57BL/6 mice were fasted for six hours prior to IP injection of GO-CoA-Tat or D4-Tat ("D4" disclosed as SEQ ID NO: 2). For each time point, blood was sampled by transcardial puncture. Blood samples were collected in tubes containing EDTA and 1 mM p-hydroxymercuribenzoic acid (PHMB). Samples were centrifuged at 3,500 rpm for 10 minutes at +4° C. and then supernatants were transferred into separate tubes. Immediately 100 µl of 1N HCl per mL of cell lysate was then added and tubes were centrifuged at 3,500 rpm for 5 minutes at +4° C. Supernatants were transferred to cryovials and stored at −80° C. Serum levels of desacyl- and acyl-ghrelin were determined by ELISA (Alpco Diagnostics). For diabetic outcomes, the above protocol was followed with the exception that an oral glucose challenge (1 g/kg) was administered thirty minutes prior to blood sampling. For diabetic outcomes compound was administered to non-fasted mice 6 hours prior to an 18 hour fast, at which time a 2.5 g/kg intraperitoneal glucose tolerance test (IP-GTT) was performed on conscious mice. Blood was sampled from the tail vein at 0, 15, 30, 60 and 120 min post IP-GTT. Glucose was measured with a glucometer (LifeScan OneTouch) and insulin values were assessed by ELISA (Alpco Diagnostics). To assess the effects of daily IP administration of GO-CoA-Tat on body composition, 8 week C57BL6J mice (Jackson Laboratories, Bar Harbor, Me.) of the same litter were weight matched into two groups 23.2+/−1.2 g (n=3) and 22.6+/−2.2 (n=3) and were placed on a high fat diet 7 days prior to intervention. On day 8, mice were continued on a high fat diet but began receiving a 29 mg/kg dose of GO-CoA-Tat (n=3) or a molar equivalent dose of D4-Tat ("D4" disclosed as SEQ ID NO: 2) peptide (n=3). Mice were monitored for two weeks in direct calorimetry cages (Nalgene) with daily measurements of food and water intake and feces and urine production. Further, body profile of mice was assessed with QNMR every three days (EchoMRI). For each body measurement, the average of three separate scans was obtained. For fecal analysis, feces was collected over a period of three days and stored in 1.5 ml ultracentrifuge tubes. Feces was rehydrated and total feces from GO-CoA-Tat (n=4) and D4-Tat ("D4" disclosed as SEQ ID NO: 2) (n=4) was compared with four separate scans.

Example 14

QRT-PCR

Islets were isolated as described in Song et al. (41) after collagenase and DNaseI digestion of the pancreas. Total RNA was extracted using Trizol. RT-PCR was performed using the one-tube RT-PCR Sybr green mix (BioRad) according to standard protocols. Fold changes in expression levels were calculated using the DDCT method. Duplicate results were analyzed using Student's t-Test. Primers used for RT-PCR:

```
                        (SEQ ID NO: 9)
Insulin Fw:    CGAGGCTTCTTCTACACACC;

(SEQ ID NO: 10)
Insulin Rv:    GAGGGAGCAGATGCTGGT (SEQ ID NO: 11)
Glucagon Fw:   CCACTCACAGGGCACATTCA;

(SEQ ID NO: 12)
Glucagon Rv:   GTCCCTGGTGGCAAGATTGT (SEQ ID NO: 13)
GHSR Fw:       ACCTGCTCTGCAAACTCTTCCAGT;

(SEQ ID NO: 14)
GHSR Rv:       CAAACACCACCACAGCAAGCATCT (SEQ ID NO: 15)
Ghrelin Fw:    ACTCAGCATGCTCTGGATGGACA;

(SEQ ID NO: 16)
Ghrelin Rv:    ATGCCAACATCGAAGGGAGCATTG (SEQ ID NO: 17)
UCP2-001 Fw:   TGGTTGGTTTCAAGGCCACAGATG;

(SEQ ID NO: 18)
UCP2-001 Rv:   TCTCGTGCAATGGTCTTGTAGGCT (SEQ ID NO: 19)
36B4 Fw:       TGTTTGACAACGGCAGCATTT;

(SEQ ID NO: 20)
36B4 Rv:       CCGAGGCAACAGTTGGGTA
```

Example 15

Immunohistochemistry

Mouse pancreas or human islets were fixed in 10% buffered formalin or Bouin's solution, paraffin embedded and 5 μm sections were prepared. After dewaxing, rehydration, and antigen retrieval in citrate buffer, immunostaining was performed with guinea pig anti-insulin (Abeam), rabbit anti-ghrelin (Abeam) and chicken anti-GHSR (Chemicon). Appropriate fluorescence-tagged secondary antibodies (Donkey anti guinea pig Cy3, Donkey anti-rabbit FITC, Jackson Immunoresearch) were used for antigen localization. Nuclei were counterstained using DAPI contained in mounting medium (Vector Biolabs). A Zeiss Axioskop equipped with a CCD digital camera and an Apotome optical sectioning device connected to a digital image processor for pseudocoloring were used for image preparation.

Example 16

Figure 11:
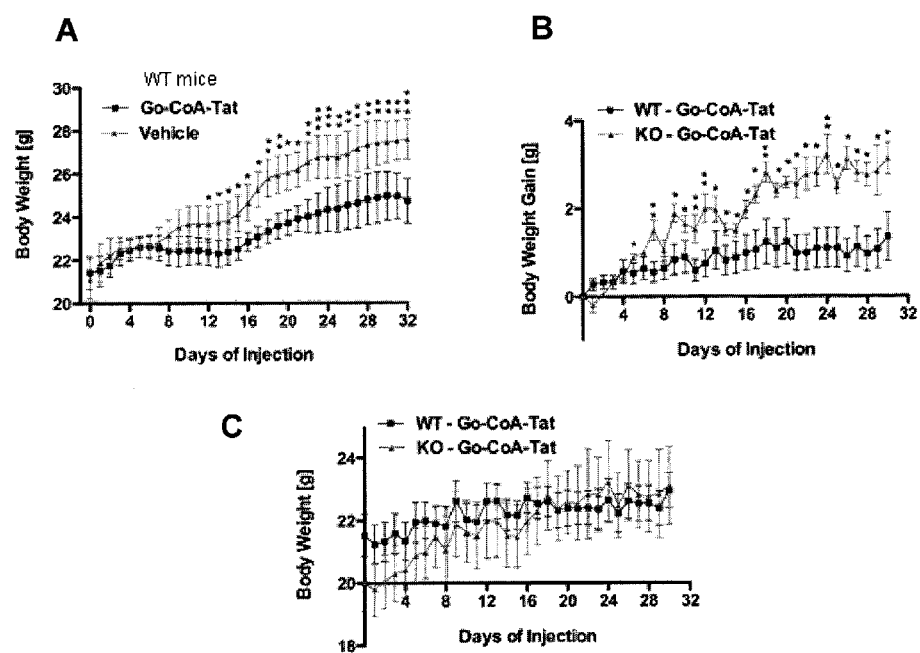
FIGS. 11A-11C: Weight gain in wild type or ghrelin knockout mice on a medium chain triglyceride diet, with or without GOAT antagonist. The GOAT inhibitor GO-CoA-Tat affects the weight of wild type but not genetically altered (ghrelin knockout) mice, confirming the targeting of the ghrelin pathway

Long-term Studies on Ghrelin-Deficient (Ghrelin KO) and Wild-Type (WT) Mice on MCT Diet Ghrelin-deficient mice were generated by using the high-throughput VelociGene gene-targeting system, as described previously (42). All animals were maintained on a 12:12-h light-dark cycle at 22° C. and fed a diet enriched in medium chain triglycerides (MCT)-(10% MCT, 40% sucrose, Teklad TD 08622) with free access to food and water. 40 mg/kg Go-CoA-TAT was administered to WT and KO mice and vehicle was administered to WT mice. Whole body composition (fat and lean mass) was measured using NMR technology (EchoMRI, Houston, Tex.) every 3-4 days and daily weight measurements were taken. Results are presented in FIG. 11.

Example 17

Glucose Tolerance Test in Ghrelin KO and WT Mice

Figure 12:
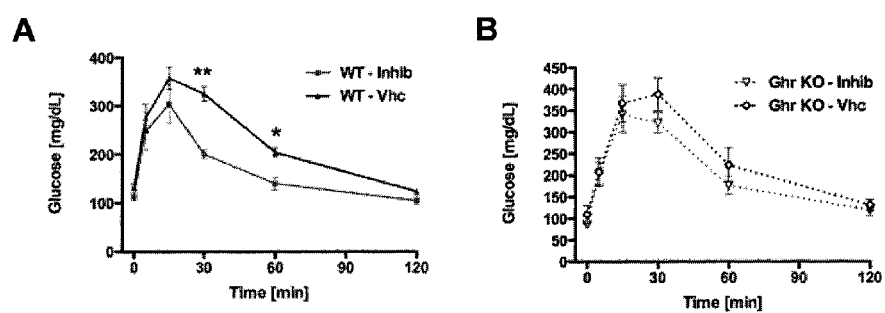
FIGS. 12A-12B: Glucose tolerance test in wild type and ghrelin knockout mice given GOAT antagonist. The GOAT inhibitor GO-CoA-Tat affects the glucose levels of wild type but not genetically altered (ghrelin knockout) mice, confirming the targeting of the ghrelin pathway.

For diabetic outcomes 40 mg/kg Go-CoA-Tat ("inhib" in FIG. 12) was administered to non-fasted wt mice (n=5) and ghrelin-ko mice (n=5) and vehicle (double distilled water; "Vhc" in FIG. 12) was administered to age matched wt mice (n=5) and ghrelin-ko mice (n=5) 6 hours prior to an 18 hour fast. After an 18 hour fast a 2.5 g/kg intraperitoneal glucose tolerance test (IP-GTT) was performed on conscious mice. Blood was sampled from the tail vein at 0, 15, 30, 60 and 120 min post IP-GTT. Glucose was measured with a glucometer (LifeScan OneTouch).

Example 18

Cross-Linking of Photoactivatable GO-CoA-Tat Analogs and Solubilized GOAT

Figure 13:
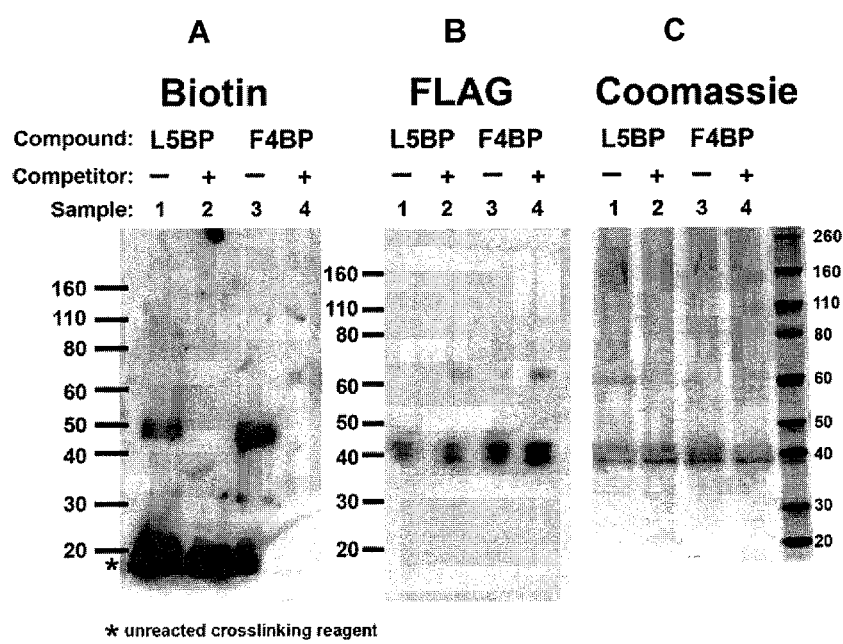
FIGS. 13A-13C: Photoactivatable GO-CoA-Tat analogs can cross-link solubilized GOAT. Two photoactivatable versions of GO-CoA-Tat can directly bind and chemically crosslink to GOAT.

FLAG-GOAT enzyme was overproduced in SF9 cells, solubilized with detergent, and treated with UV light in the presence of a benzoyl-phenylalanine- and biotin-containing analog of GO-CoA-Tat (5 uM). These led to crosslinking as shown in the Biotin blot (FIG. 13A), which could be blocked with standard GO-CoA-Tat (100 uM). FLAG (FIG. 13B) and Coomassie (FIG. 13C) gels indicate even loading in these lanes.

Example 19

GOAT Inhibitor Effects on IGF-1

Figure 14:
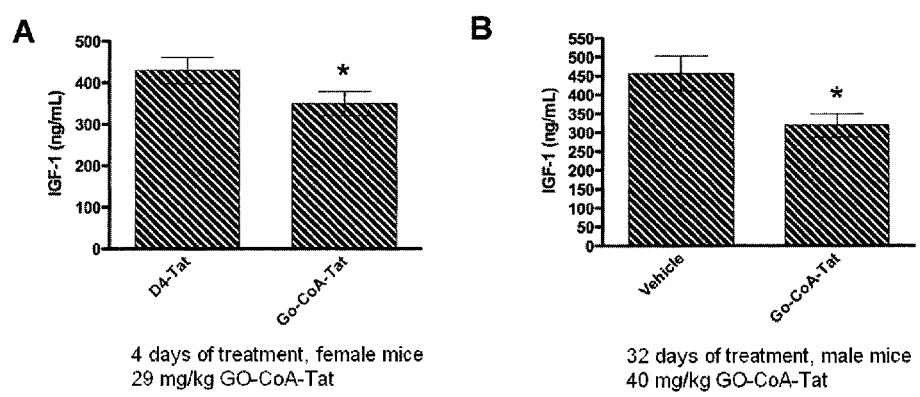
FIGS. 14A-14B: GOAT inhibitor suppresses blood IGF1 levels in male and female mice. This is consistent with an effect on acyl-ghrelin. Figures disclose "D4" disclosed as SEQ ID NO: 2.

Blood was collected from transcardial puncture using EDTA-coated Microvette tubes and immediately chilled on ice. After 15 min of centrifugation at 3,000 g and 4° C., plasma was stored at −80° C. For quantification of plasma IGF-1 levels a commercially available assay was used (R&D Systems, Minneapolis, Minn.). This assay is validated for the measurement of IGF-1 in nonacidified plasma samples and does not require protein extraction. The assay was performed according to the assay manufacturer's instructions. Results are presented in FIG. 14.

The embodiments illustrated and discussed in this specification are intended only to teach those skilled in the art the best way known to the inventors to make and use the invention. Nothing in this specification should be construed as limiting the scope of the present invention. All examples presented are representative and non-limiting. The above-described embodiments of the invention may be modified or varied without departing from the invention, as appreciated by those skilled in the art in light of the above teachings. It is therefore to be understood that, within the scope of the claims and their equivalents, the invention may be practiced otherwise than as specifically described.

REFERENCES

1. M. Rosenbaum et al., *J Clin Endocrinol Metab* 81, 3424 (September, 1996).
2. M. Kojima et al., *Nature* 402, 656 (Dec. 9, 1999).

3. M. Tschop, D. L. Smiley, M. L. Heiman, *Nature* 407, 908 (Oct. 19, 2000).
4. A. M. Wren et al., *Diabetes* 50, 2540 (November, 2001).
5. J. M. Zigman et al., *J Clin Invest* 115, 3564 (December, 2005).
6. T. Yada et al., *Curr Diabetes Rev* 4, 18 (February, 2008).
7. K. Dezaki, M. Kakei, T. Yada, *Diabetes* 56, 2319 (September, 2007).
8. Y. Sun, M. Asnicar, P. K. Saha, L. Chan, R. G. Smith, *Cell Metab* 3, 379 (May, 2006).
9. O. Gualillo, F. Lago, C. Dieguez, *Trends Pharmacol Sci* 29, 398 (August, 2008).
10. J. A. Gutierrez et al., *Proc Natl Acad Sci USA* 105, 6320 (Apr. 29, 2008).
11. J. Yang, M. S. Brown, G. Liang, N. V. Grishin, J. L. Goldstein, *Cell* 132, 387 (Feb. 8, 2008).
12. O. D. Lau et al., *Mol Cell* 5, 589 (March, 2000).
13. K. Parang et al., *Nat Struct Biol* 8, 37 (January, 2001).
14. J. Yang, T. J. Zhao, J. L. Goldstein, M. S. Brown, *Proc Natl Acad Sci USA* 105, 10750 (Aug. 5, 2008).
15. F. C. Tinsley, G. Z. Taicher, M. L. Heiman, *Obes Res* 12, 150 (January, 2004).
16. K. Dezaki, H. Sone, T. Yada, *Pharmacol Ther* 118, 239 (May, 2008).
17. C. Gauna et al., *J Clin Endocrinol Metab* 90, 1055 (February, 2005).
18. C. Gauna et al., *J Clin Endocrinol Metab* 89, 5035 (October, 2004).
19. C. Y. Zhang et al., *Cell* 105, 745 (Jun. 15, 2001).
20. J. W. Joseph et al., *Diabetes* 51, 3211 (November, 2002).
21. Z. B. Andrews et al., *Nature* 454, 846 (Aug. 14, 2008).
22. T. N. Wang et al., *Int J Obes* (Lond) 31, 1746 (November, 2007).
23. H. Esterbauer et al., *Nat Genet.* 28, 178 (June, 2001).
24. M. Sasahara et al., *Diabetes* 53, 482 (February, 2004).
25. F. Broglio et al., *J Clin Endocrinol Metab* 89, 3062 (June, 2004).
26. H. Ariyasu et al., *Endocrinology* 146, 355 (January, 2005).
27. W. Zhang, B. Chai, J. Y. Li, H. Wang, M. W. Mulholland, *Endocrinology* 149, 4710 (September, 2008).
28. K. Hofmann, *Trends Biochem Sci* 25, 111 (March, 2000).
29. A. Turkish, S. L. Sturley, *Am J Physiol Gastrointest Liver Physiol* 292, G953 (April, 2007).
30. INUI et al., FASEB, 18 (3): 439. (2004).
31. Levin et al., JCEM 91 (9): 3296. (2006).
32. Murray, C D R et al., Gut 2005; 54:1693-1698.
33. O. D. Lau et al., *Mol Cell* 5, 589 (March, 2000).
34. A. C. Hines, P. A. Cole, *Bioorg Med Chem Lett* 14, 2951 (Jun. 7, 2004).
35. W. Wang, B. A. Malcolm, *Biotechniques* 26, 680 (April, 1999).
36. J. Yang, T. J. Zhao, J. L. Goldstein, M. S. Brown, *Proc Natl Acad Sci USA* 105, 10750 (Aug. 5, 2008).
37. L. M. Szewczuk et al., *J Med Chem* 50, 5330 (Nov. 1, 2007).
38. P. R. Thompson et al., *Nat Struct Mol Biol* 11, 308 (April, 2004).
39. Y. Zheng et al., *Biochemistry* 44, 10501 (Aug. 9, 2005).
40. J. De Angelis, J. Gastel, D. C. Klein, P. A. Cole, *J Biol Chem* 273, 3045 (Jan. 30, 1998).
41. W. J. Song et al., *Diabetes* 57, 2371 (September, 2008).
42. Valenzuela D M et al., High-throughput engineering of the mouse genome coupled with high-resolution expression analysis. Nat Biotechnol 21, 652-659 (2003).

The invention claimed is:

1. A compound of the formula (I):

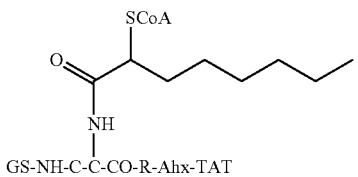

GS-NH-C-C-CO-R-Ahx-TAT  (I)

wherein R is absent, or is an organic moiety selected from the group consisting of a substituted or unsubstituted alkyl group, and a substituted or unsubstituted peptide chain and wherein TAT is the peptide shown in SEQ ID NO:3.

2. The compound of claim 1, wherein R is a peptide of 12 amino acid residues so that the peptide GS to TAT is represented by SEQ ID NO:21.

3. The compound of claim 1, wherein R is a peptide of 7 amino acid residues corresponding to ghrelin residues 4 through 10 so that the peptide GS to TAT is represented by SEQ ID NO:22.

4. The compound of claim 1, wherein R is a peptide of 12 amino acid residues corresponding to ghrelin residues 4 through 15 so that the peptide GS to TAT is represented by SEQ ID NO:23.

5. A composition comprising the compound of claim 1 and a pharmaceutically acceptable excipient or carrier.

6. A method for preparing the compound of one of claim 1, comprising the steps of:
    providing a ghrelin peptide sequence comprising from 3 to 15 N-terminal amino acid residues, wherein the serine residue at the 3 position is replaced with alloc-protected 1,2-diaminopropionic acid and wherein D4-Tat ("D4" disclosed as SEQ ID No:26) is bound to one end of the peptide sequence (SEQ ID NO: 26);

combining the ghrelin peptide sequence with Pd(PPh$_3$)$_4$ palladium reagent, n-bromo octanoic anhydride and Reagent K in one or more reaction vessels to obtain a bromo-octanoylated intermediate; and combining the bromo-octanoylated intermediate with coenzyme A.

7. A method for treating obesity comprising administering to a subject a composition comprising a therapeutically effective amount of the composition of claim 3, wherein Xaa at position 11 of SEQ ID NO:22 is Ahx.

8. The method of claim 7, wherein administering the composition brings about a greater loss of fat mass than lean mass in the subject.

9. The method of claim 7, wherein administering the composition brings about an increase in the ratio of ghrelin to acyl-ghrelin in the subject.

10. The method of claim 7, wherein the therapeutically effective amount is at least about 5 mg/kg subject body weight.

11. The method of claim 7, wherein the therapeutically effective amount is at least about 25 mg/kg subject body weight.

12. A method for treating Type II diabetes comprising administering to a subject a composition comprising a therapeutically effective amount of the composition of claim 3, wherein Xaa at position 11 of SEQ ID NO:22 is Ahx.

13. The method of claim 12, wherein administering the composition brings about an increased production of insulin in the subject.

14. The method of claim 12, wherein administering the composition brings about a reduction in uncoupling-protein 2 (UCP-2) mRNA levels in the subject.

15. The method of claim 12, wherein the therapeutically effective amount is at least about 5 mg/kg subject body weight.

16. The method of claim 12, wherein the therapeutically effective amount is at least about 25 mg/kg subject body weight.

17. A kit comprising a composition comprising at least one dose of a therapeutically effective amount of the compound of claim 1.

* * * * *

SEQUENCE LISTING

```
<160> NUMBER OF SEQ ID NOS: 33

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (4)..(23)
<223> OTHER INFORMATION: Any amino acid and this region may encompass
      0-20 residues
<220> FEATURE:
<221> NAME/KEY: MOD_RES
<222> LOCATION: (24)..(24)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 1

Gly Ser Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Tyr Gly Arg Lys Lys Arg Arg Gln
            20                  25                  30

Arg Arg Arg
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Asp Asp Asp
1

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Arg Lys Lys Arg Arg Gln Arg Arg Arg
1               5                   10

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Lys(Biotin)

<400> SEQUENCE: 4

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Lys Gly
            20                  25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttacaaggg caccgcttag                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caaggcatct tctggcattt                                            20

<210> SEQ ID NO 7
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccaccatgg attggctcca gctc                                            24

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagatgaagg gcagggaaa                                                  19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaggcttct tctacacacc                                                 20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagggagcag atgctggt                                                   18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccactcacag ggcacattca                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtccctggtg gcaagattgt                                                 20

<210> SEQ ID NO 13
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acctgctctg caaactcttc cagt                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caaacaccac cacagcaagc atct                                              24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actcagcatg ctctggatgg aca                                               23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgccaacat cgaagggagc attg                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tggttggttt caaggccaca gatg                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctcgtgcaa tggtcttgta ggct                                              24

<210> SEQ ID NO 19
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 19
tgtttgacaa cggcagcatt t                                            21

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgaggcaac agttgggta                                               19

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (4)..(15)
<223> OTHER INFORMATION: Any amino acid and this region may encompass
      1-12 residues
<220> FEATURE:
<221> NAME/KEY: MOD_RES
<222> LOCATION: (16)..(16)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 21

Gly Ser Xaa Xaa Xaa Xaa Xaa Xaa Xaa Xaa Xaa Xaa Xaa Xaa Xaa Xaa
1               5                   10                  15

Tyr Gly Arg Lys Lys Arg Arg Gln Arg Arg Arg
            20                  25

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (11)..(11)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 22

```
Gly Ser Xaa Phe Leu Ser Pro Glu His Gln Xaa Tyr Gly Arg Lys Lys
1               5                   10                  15

Arg Arg Gln Arg Arg Arg
            20
```

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (16)..(16)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 23

```
Gly Ser Xaa Phe Leu Ser Pro Glu His Gln Arg Val Gln Gln Arg Xaa
1               5                   10                  15

Tyr Gly Arg Lys Lys Arg Arg Gln Arg Arg Arg
            20                  25
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (6)..(6)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 24

```
Gly Ser Xaa Phe Leu Xaa Tyr Gly Arg Lys Lys Arg Arg Gln Arg Arg
1               5                   10                  15

Arg
```

<210> SEQ ID NO 25
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (29)..(29)
<223> OTHER INFORMATION: Aminohexanoic acid, glycine, amino propionic

```
      acid, amino butyric acid, aminopentanoic acid or not present
<220> FEATURE:
<223> OTHER INFORMATION: See specification as filed for detailed
      description of substitutions and preferred embodiments

<400> SEQUENCE: 25

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Lys Xaa Tyr Gly Arg
            20                  25                  30

Lys Lys Arg Arg Gln Arg Arg Arg
            35                  40

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: 1,2-diaminopropionic acid

<400> SEQUENCE: 26

Gly Ser Xaa Phe Leu Ser Pro Glu His Gln Arg Val Gln Gln Arg Asp
1               5                   10                  15

Asp Asp Asp Tyr Gly Arg Lys Lys Arg Arg Gln Arg Arg Arg
            20                  25                  30

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated

<400> SEQUENCE: 27

Asp Asp Asp Asp Tyr Gly Arg Lys Lys Arg Arg Gln Arg Arg Arg
1               5                   10                  15

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (11)..(11)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 28

Gly Ser Xaa Phe Leu Ser Pro Glu His Gln Xaa Tyr Gly Arg Lys Lys
1               5                   10                  15
```

-continued

Arg Arg Gln Arg Arg Arg
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (11)..(11)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 29

Gly Ser Xaa Phe Leu Ser Pro Glu His Gln Xaa Tyr Gly Arg Lys Lys
1               5                   10                  15

Arg Arg Gln Arg Arg Arg
            20

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (4)..(4)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 30

Gly Ser Xaa Xaa Tyr Gly Arg Lys Lys Arg Arg Gln Arg Arg Arg
1               5                   10                  15

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (11)..(11)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

```
-continued

<400> SEQUENCE: 31

Gly Ser Xaa Phe Leu Ser Pro Glu His Gln Xaa Tyr Gly Arg Lys Lys
1               5                   10                  15

Arg Arg Gln Arg Arg Arg
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid
<220> FEATURE:
<221> NAME/KEY: MOD_RES
<222> LOCATION: (11)..(11)
<223> OTHER INFORMATION: Aminohexanoic acid, glycine, amino propionic
      acid, amino butyric acid, aminopentanoic acid or not present
<220> FEATURE:
<223> OTHER INFORMATION: See specification as filed for detailed
      description of substitutions and preferred embodiments

<400> SEQUENCE: 32

Gly Ser Xaa Phe Leu Ser Pro Glu His Gln Xaa Tyr Gly Arg Lys Lys
1               5                   10                  15

Arg Arg Gln Arg Arg Arg
            20

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1,2-diaminopropionic acid

<400> SEQUENCE: 33

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```